United States Patent
PVR

(10) Patent No.: US 10,849,630 B2
(45) Date of Patent: *Dec. 1, 2020

(54) REPOSABLE MULTI-FIRE SURGICAL CLIP APPLIER

(71) Applicant: Covidien LP, Mansfield, MA (US)

(72) Inventor: Mohan P V R, Hyderabad (IN)

(73) Assignee: COVIDIEN LP, Mansfield, MA (US)

( * ) Notice: Subject to any disclaimer, the term of this patent is extended or adjusted under 35 U.S.C. 154(b) by 204 days.

This patent is subject to a terminal disclaimer.

(21) Appl. No.: 16/142,145

(22) Filed: Sep. 26, 2018

(65) Prior Publication Data

US 2019/0175188 A1 Jun. 13, 2019

Related U.S. Application Data

(60) Provisional application No. 62/598,437, filed on Dec. 13, 2017.

(51) Int. Cl.
*A61B 17/128* (2006.01)
*A61B 34/35* (2016.01)
(Continued)

(52) U.S. Cl.
CPC .......... *A61B 17/1285* (2013.01); *A61B 34/35* (2016.02); *A61B 2017/0023* (2013.01);
(Continued)

(58) Field of Classification Search
CPC .......................... A61B 17/128; A61B 17/1285
See application file for complete search history.

(56) References Cited

U.S. PATENT DOCUMENTS

| 3,120,230 A | 2/1964 | Skold |
| 3,363,628 A | 1/1968 | Wood |

(Continued)

FOREIGN PATENT DOCUMENTS

| AU | 2013254887 A1 | 11/2013 |
| CA | 1163889 A | 3/1984 |

(Continued)

OTHER PUBLICATIONS

Chinese First Office Action corresponding to Chinese Appln. No. CN 2014104295806 dated Aug. 31, 2017.

(Continued)

*Primary Examiner* — Katherine M Shi
*Assistant Examiner* — Lindsey Bachman

(57) ABSTRACT

A reposable surgical clip applier includes a handle assembly, a shaft assembly releasably engagable with the handle assembly, and a clip cartridge assembly releasably engagable within the shaft assembly. The handle assembly includes at least one handle, a proximal drive member, a proximal pusher, and a handle spring assembly configured to bias the handle(s) towards a spaced-apart position. When the reposable surgical clip applier is assembled, the proximal drive member is positioned proximally adjacent an inner drive assembly of the shaft assembly such that movement of the handle(s) towards an approximated position actuates a jaw assembly of the shaft assembly. When the reposable surgical clip applier is assembled, the proximal pusher is positioned proximally adjacent a distal pusher of the clip cartridge assembly such that movement of the handle(s) towards the spaced-apart position loads a distal-most surgical clip from the clip cartridge assembly into the jaw assembly.

16 Claims, 17 Drawing Sheets

(51) Int. Cl.
*A61B 17/00* (2006.01)
*A61B 90/00* (2016.01)
(52) U.S. Cl.
CPC .............. *A61B 2017/0046* (2013.01); *A61B 2017/00367* (2013.01); *A61B 2017/00477* (2013.01); *A61B 2090/0803* (2016.02); *A61B 2090/0813* (2016.02); *A61B 2090/0814* (2016.02)

(56) References Cited

U.S. PATENT DOCUMENTS

| | | |
|---|---|---|
| 3,638,847 A | 2/1972 | Noiles et al. |
| 3,675,688 A | 7/1972 | Bryan et al. |
| 3,735,762 A | 5/1973 | Bryan et al. |
| 3,867,944 A | 2/1975 | Samuels |
| 4,226,242 A | 10/1980 | Jarvik |
| 4,242,902 A | 1/1981 | Green |
| 4,296,751 A | 10/1981 | Blake, III et al. |
| 4,372,316 A | 2/1983 | Blake, III et al. |
| 4,408,603 A | 10/1983 | Blake, III et al. |
| 4,412,539 A | 11/1983 | Jarvik |
| 4,418,694 A | 12/1983 | Beroff et al. |
| 4,471,780 A | 9/1984 | Menges et al. |
| 4,480,640 A | 11/1984 | Becht |
| 4,480,641 A | 11/1984 | Failla et al. |
| 4,487,204 A | 12/1984 | Hrouda |
| 4,487,205 A | 12/1984 | Di Giovanni et al. |
| 4,491,133 A | 1/1985 | Menges et al. |
| 4,492,232 A | 1/1985 | Green |
| 4,498,476 A | 2/1985 | Cerwin et al. |
| 4,500,024 A | 2/1985 | DiGiovanni et al. |
| 4,509,518 A | 4/1985 | McGarry et al. |
| 4,512,345 A | 4/1985 | Green |
| 4,522,207 A | 6/1985 | Klieman et al. |
| 4,532,925 A | 8/1985 | Blake, III |
| 4,534,351 A | 8/1985 | Rothfuss et al. |
| 4,545,377 A | 10/1985 | Cerwin et al. |
| 4,549,544 A | 10/1985 | Favaron |
| 4,556,058 A | 12/1985 | Green |
| 4,557,263 A | 12/1985 | Green |
| 4,562,839 A | 1/1986 | Blake, III et al. |
| 4,572,183 A | 2/1986 | Juska |
| 4,576,165 A | 3/1986 | Green et al. |
| 4,576,166 A | 3/1986 | Montgomery et al. |
| 4,590,937 A | 5/1986 | Deniega |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery et al. |
| 4,662,374 A | 5/1987 | Blake, III |
| 4,671,278 A | 6/1987 | Chin |
| 4,671,282 A | 6/1987 | Tretbar |
| 4,674,504 A | 6/1987 | Klieman et al. |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters et al. |
| 4,726,372 A | 2/1988 | Perlin |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,796,625 A | 1/1989 | Kees, Jr. |
| 4,799,481 A | 1/1989 | Transue et al. |
| 4,815,466 A | 3/1989 | Perlin |
| 4,821,721 A | 4/1989 | Chin et al. |
| 4,822,348 A | 4/1989 | Casey |
| 4,834,096 A | 5/1989 | Oh et al. |
| 4,850,355 A | 7/1989 | Brooks et al. |
| 4,854,317 A | 8/1989 | Braun |
| 4,856,517 A | 8/1989 | Collins et al. |
| 4,929,239 A | 5/1990 | Braun |
| 4,931,058 A | 6/1990 | Cooper |
| 4,934,364 A | 6/1990 | Green |
| 4,957,500 A | 9/1990 | Liang et al. |
| 4,966,603 A | 10/1990 | Focelle et al. |
| 4,967,949 A | 11/1990 | Sandhaus |
| 4,983,176 A | 1/1991 | Cushman et al. |
| 4,988,355 A | 1/1991 | Leveen et al. |
| 5,002,552 A | 3/1991 | Casey |
| 5,026,379 A | 6/1991 | Yoon |
| 5,030,224 A | 7/1991 | Wright et al. |
| 5,030,226 A | 7/1991 | Green et al. |
| 5,032,127 A | 7/1991 | Frazee et al. |
| 5,035,692 A | 7/1991 | Lyon et al. |
| 5,047,038 A | 9/1991 | Peters et al. |
| 5,049,152 A | 9/1991 | Simon et al. |
| 5,049,153 A | 9/1991 | Nakao et al. |
| 5,053,045 A | 10/1991 | Schmidt et al. |
| 5,059,202 A | 10/1991 | Liang et al. |
| 5,062,563 A | 11/1991 | Green et al. |
| 5,062,846 A | 11/1991 | Oh et al. |
| 5,078,731 A | 1/1992 | Hayhurst |
| 5,084,057 A | 1/1992 | Green et al. |
| 5,100,416 A | 3/1992 | Oh et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,122,150 A * | 6/1992 | Puig .................. A61B 17/1285 606/139 |
| 5,127,915 A | 7/1992 | Mattson |
| 5,129,885 A | 7/1992 | Green et al. |
| 5,156,608 A | 10/1992 | Troidl et al. |
| 5,160,339 A | 11/1992 | Chen et al. |
| 5,163,945 A | 11/1992 | Ortiz et al. |
| 5,171,247 A | 12/1992 | Hughett et al. |
| 5,171,249 A | 12/1992 | Stefanchik et al. |
| 5,171,250 A | 12/1992 | Yoon |
| 5,171,251 A | 12/1992 | Bregen et al. |
| 5,171,252 A | 12/1992 | Friedland |
| 5,171,253 A | 12/1992 | Klieman |
| 5,192,288 A | 3/1993 | Thompson et al. |
| 5,197,970 A | 3/1993 | Green et al. |
| 5,199,566 A | 4/1993 | Ortiz et al. |
| 5,201,746 A | 4/1993 | Shichman |
| 5,201,900 A | 4/1993 | Nardella |
| 5,207,691 A | 5/1993 | Nardella |
| 5,207,692 A | 5/1993 | Kraus et al. |
| 5,217,473 A | 6/1993 | Yoon |
| 5,219,353 A | 6/1993 | Garvey, III et al. |
| 5,246,450 A | 9/1993 | Thornton et al. |
| 5,269,792 A | 12/1993 | Kovac et al. |
| 5,281,228 A | 1/1994 | Wolfson |
| 5,282,807 A | 2/1994 | Knoepfler |
| 5,282,808 A | 2/1994 | Kovac et al. |
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |
| 5,330,442 A | 7/1994 | Green et al. |
| 5,330,487 A | 7/1994 | Thornton et al. |
| 5,340,360 A | 8/1994 | Stefanchik |
| 5,342,373 A | 8/1994 | Stefanchik et al. |
| 5,354,304 A * | 10/1994 | Allen .................. A61B 17/122 227/901 |
| 5,354,306 A | 10/1994 | Garvey, III et al. |
| 5,356,064 A | 10/1994 | Green et al. |
| 5,359,993 A | 11/1994 | Slater et al. |

(56) References Cited

U.S. PATENT DOCUMENTS

| | | |
|---|---|---|
| 5,366,458 A | 11/1994 | Korthoff et al. |
| 5,366,459 A | 11/1994 | Yoon |
| 5,368,600 A | 11/1994 | Failla et al. |
| 5,381,943 A | 1/1995 | Allen et al. |
| 5,382,253 A | 1/1995 | Hogendijk |
| 5,382,254 A | 1/1995 | McGarry et al. |
| 5,382,255 A | 1/1995 | Castro et al. |
| 5,383,880 A | 1/1995 | Hooven |
| 5,383,881 A | 1/1995 | Green et al. |
| 5,395,375 A | 3/1995 | Turkel et al. |
| 5,395,381 A | 3/1995 | Green et al. |
| 5,403,327 A | 4/1995 | Thornton et al. |
| 5,409,498 A * | 4/1995 | Braddock .......... A61B 17/1285 227/901 |
| 5,413,584 A | 5/1995 | Schulze |
| 5,423,835 A | 6/1995 | Green et al. |
| 5,425,740 A | 6/1995 | Hutchinson, Jr. |
| 5,431,667 A | 7/1995 | Thompson et al. |
| 5,431,668 A | 7/1995 | Burbank, III et al. |
| 5,431,669 A | 7/1995 | Thompson et al. |
| 5,439,468 A | 8/1995 | Schulze et al. |
| 5,441,509 A | 8/1995 | Vidal et al. |
| 5,447,513 A | 9/1995 | Davison et al. |
| 5,448,042 A | 9/1995 | Robinson et al. |
| 5,449,365 A | 9/1995 | Green et al. |
| 5,462,555 A | 10/1995 | Bolanos et al. |
| 5,462,558 A | 10/1995 | Kolesa et al. |
| 5,464,416 A | 11/1995 | Steckel |
| 5,474,566 A | 12/1995 | Alesi et al. |
| 5,474,567 A | 12/1995 | Stefanchik et al. |
| 5,474,572 A | 12/1995 | Hayhurst |
| 5,487,499 A | 1/1996 | Sorrentino et al. |
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,520,701 A | 5/1996 | Lerch |
| 5,527,318 A | 6/1996 | McGarry |
| 5,527,319 A | 6/1996 | Green et al. |
| 5,527,320 A | 6/1996 | Carruthers et al. |
| 5,542,949 A | 8/1996 | Yoon |
| 5,547,474 A | 8/1996 | Kloeckl et al. |
| 5,562,655 A | 10/1996 | Mittelstadt et al. |
| 5,569,274 A | 10/1996 | Rapacki et al. |
| 5,571,121 A | 11/1996 | Heifetz |
| 5,575,802 A | 11/1996 | McQuilkin et al. |
| 5,582,615 A | 12/1996 | Foshee et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A | 2/1997 | Fogelberg et al. |
| 5,601,574 A | 2/1997 | Stefanchik et al. |
| 5,607,436 A | 3/1997 | Pratt et al. |
| 5,618,291 A | 4/1997 | Thompson et al. |
| 5,618,306 A | 4/1997 | Roth et al. |
| 5,620,452 A | 4/1997 | Yoon |
| 5,626,585 A | 5/1997 | Mittelstadt et al. |
| 5,626,586 A | 5/1997 | Pistl et al. |
| 5,626,587 A | 5/1997 | Bishop et al. |
| 5,626,592 A | 5/1997 | Phillips et al. |
| RE35,525 E | 6/1997 | Stefanchik et al. |
| 5,634,930 A | 6/1997 | Thornton et al. |
| 5,643,291 A | 7/1997 | Pier et al. |
| 5,645,551 A | 7/1997 | Green et al. |
| 5,645,553 A | 7/1997 | Kolesa et al. |
| 5,649,937 A | 7/1997 | Bito et al. |
| 5,653,720 A | 8/1997 | Johnson et al. |
| 5,662,662 A | 9/1997 | Bishop et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier et al. |
| 5,695,505 A | 12/1997 | Yoon |
| 5,697,938 A | 12/1997 | Jensen et al. |
| 5,697,942 A | 12/1997 | Palti |
| 5,700,270 A | 12/1997 | Peyser et al. |
| 5,700,271 A | 12/1997 | Whitfield et al. |
| 5,702,048 A | 12/1997 | Eberlin |
| 5,709,706 A | 1/1998 | Kienzle et al. |
| 5,713,911 A | 2/1998 | Racenet et al. |
| 5,713,912 A | 2/1998 | Porter |
| 5,720,756 A | 2/1998 | Green et al. |
| 5,722,982 A | 3/1998 | Ferreira et al. |
| 5,725,537 A | 3/1998 | Green et al. |
| 5,725,538 A | 3/1998 | Green et al. |
| 5,725,542 A | 3/1998 | Yoon |
| 5,733,295 A | 3/1998 | Back et al. |
| 5,743,310 A | 4/1998 | Moran |
| 5,749,881 A | 5/1998 | Sackier et al. |
| 5,755,726 A | 5/1998 | Pratt et al. |
| 5,766,189 A | 6/1998 | Matsuno |
| 5,769,857 A | 6/1998 | Reztzov et al. |
| 5,772,673 A | 6/1998 | Cuny et al. |
| 5,776,146 A | 7/1998 | Sackier et al. |
| 5,776,147 A | 7/1998 | Dolendo |
| 5,779,718 A | 7/1998 | Green et al. |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sherts et al. |
| 5,792,150 A | 8/1998 | Pratt et al. |
| 5,797,922 A | 8/1998 | Hessel et al. |
| 5,810,853 A | 9/1998 | Yoon |
| 5,817,116 A | 10/1998 | Takahashi et al. |
| 5,827,306 A | 10/1998 | Yoon |
| 5,827,323 A | 10/1998 | Klieman et al. |
| 5,833,695 A | 11/1998 | Yoon |
| 5,833,696 A | 11/1998 | Whitfield et al. |
| 5,833,700 A | 11/1998 | Fogelberg et al. |
| 5,835,199 A | 11/1998 | Phillips et al. |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser et al. |
| 5,868,761 A | 2/1999 | Nicholas et al. |
| 5,876,410 A | 3/1999 | Petillo |
| 5,895,394 A | 4/1999 | Kienzle et al. |
| 5,897,565 A | 4/1999 | Foster |
| 5,904,693 A | 5/1999 | Dicesare et al. |
| 5,906,625 A | 5/1999 | Bito et al. |
| 5,913,862 A | 6/1999 | Ramsey et al. |
| 5,913,876 A | 6/1999 | Taylor et al. |
| 5,918,791 A | 7/1999 | Sorrentino et al. |
| 5,921,991 A | 7/1999 | Whitehead et al. |
| 5,921,996 A | 7/1999 | Sherman |
| 5,921,997 A | 7/1999 | Fogelberg et al. |
| 5,928,251 A | 7/1999 | Aranyi et al. |
| 5,938,667 A | 8/1999 | Peyser et al. |
| 5,951,574 A | 9/1999 | Stefanchik et al. |
| 5,972,003 A | 10/1999 | Rousseau et al. |
| 5,976,159 A | 11/1999 | Bolduc et al. |
| 5,993,465 A | 11/1999 | Shipp et al. |
| 6,004,335 A | 12/1999 | Vaitekunas et al. |
| 6,009,551 A | 12/1999 | Sheynblat |
| 6,017,358 A | 1/2000 | Yoon et al. |
| 6,044,971 A | 4/2000 | Esposito et al. |
| 6,045,560 A | 4/2000 | McKean et al. |
| 6,053,908 A | 4/2000 | Crainich et al. |
| RE36,720 E | 5/2000 | Green et al. |
| 6,059,799 A | 5/2000 | Aranyi et al. |
| 6,099,536 A | 8/2000 | Petillo |
| 6,099,537 A | 8/2000 | Sugai et al. |
| 6,139,555 A | 10/2000 | Hart et al. |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis et al. |

(56) References Cited

U.S. PATENT DOCUMENTS

| | | |
|---|---|---|
| 6,258,105 B1 | 7/2001 | Hart et al. |
| 6,261,302 B1 | 7/2001 | Voegele et al. |
| 6,273,898 B1 | 8/2001 | Kienzle et al. |
| 6,277,131 B1 | 8/2001 | Kalikow |
| 6,306,149 B1 | 10/2001 | Meade |
| 6,318,619 B1 | 11/2001 | Lee |
| 6,322,571 B1 | 11/2001 | Adams |
| 6,350,269 B1 | 2/2002 | Shipp et al. |
| 6,352,541 B1 | 3/2002 | Kienzle et al. |
| 6,391,035 B1 | 5/2002 | Appleby et al. |
| 6,423,079 B1 | 7/2002 | Blake, III |
| 6,428,548 B1 | 8/2002 | Durgin |
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 | 12/2002 | Wilk et al. |
| 6,517,536 B2 | 2/2003 | Hooven et al. |
| 6,520,972 B2 | 2/2003 | Peters |
| 6,527,786 B1 | 3/2003 | Davis et al. |
| 6,537,289 B1 | 3/2003 | Kayan et al. |
| 6,546,935 B2 | 4/2003 | Hooven |
| 6,551,333 B2 | 4/2003 | Kuhns et al. |
| 6,562,051 B1 | 5/2003 | Bolduc et al. |
| 6,569,171 B2 | 5/2003 | DeGuillebon et al. |
| 6,579,304 B1 | 6/2003 | Hart et al. |
| 6,599,298 B1 | 7/2003 | Forster et al. |
| 6,602,252 B2 | 8/2003 | Mollenauer |
| 6,607,540 B1 | 8/2003 | Shipp |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |
| 6,652,539 B2 | 11/2003 | Shipp et al. |
| 6,656,193 B2 | 12/2003 | Grant et al. |
| 6,673,083 B1 | 1/2004 | Kayan et al. |
| 6,676,659 B2 | 1/2004 | Hutchins et al. |
| 6,679,894 B2 | 1/2004 | Damarati |
| RE38,445 E | 2/2004 | Pistl et al. |
| 6,695,854 B1 | 2/2004 | Kayan et al. |
| 6,706,057 B1 | 3/2004 | Bidoia et al. |
| 6,716,226 B2 | 4/2004 | Sixto, Jr. et al. |
| 6,723,109 B2 | 4/2004 | Solingen |
| 6,733,514 B2 | 5/2004 | Miser |
| 6,743,240 B2 | 6/2004 | Smith et al. |
| 6,743,241 B2 | 6/2004 | Kerr |
| 6,773,438 B1 | 8/2004 | Knodel et al. |
| 6,773,440 B2 | 8/2004 | Gannoe et al. |
| 6,776,783 B1 | 8/2004 | Frantzen et al. |
| 6,776,784 B2 | 8/2004 | Ginn |
| 6,780,195 B2 | 8/2004 | Porat |
| 6,793,663 B2 | 9/2004 | Kneifel et al. |
| 6,793,664 B2 | 9/2004 | Mazzocchi et al. |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,821,285 B2 | 11/2004 | Laufer et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,676 B2 | 5/2005 | Zubok et al. |
| 6,896,682 B1 | 5/2005 | McClellan et al. |
| 6,896,684 B2 | 5/2005 | Monassevitch et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,916,332 B2 | 7/2005 | Adams |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B1 | 11/2005 | Suyker et al. |
| 6,966,919 B2 | 11/2005 | Sixto, Jr. et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,635 B2 | 1/2006 | Takamoto et al. |
| 7,001,399 B2 | 2/2006 | Damarati |
| 7,037,315 B2 | 5/2006 | Sancoff et al. |
| 7,041,119 B2 | 5/2006 | Green |
| 7,052,504 B2 | 5/2006 | Hughett |
| 7,056,330 B2 | 6/2006 | Gayton |
| 7,070,602 B2 | 7/2006 | Smith et al. |
| 7,108,700 B2 | 9/2006 | Chan |
| 7,108,703 B2 | 9/2006 | Danitz et al. |
| 7,141,056 B2 | 11/2006 | Manetakis |
| 7,144,402 B2 | 12/2006 | Kuester, III |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et al. |
| 7,211,092 B2 | 5/2007 | Hughett |
| 7,213,736 B2 | 5/2007 | Wales et al. |
| 7,214,230 B2 | 5/2007 | Brock et al. |
| 7,214,232 B2 | 5/2007 | Bowman et al. |
| 7,223,271 B2 | 5/2007 | Muramatsu et al. |
| 7,223,272 B2 | 5/2007 | Francese et al. |
| 7,232,445 B2 | 6/2007 | Kortenbach et al. |
| 7,238,191 B2 | 7/2007 | Bachmann |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,312,188 B2 | 12/2007 | Kiso |
| 7,316,693 B2 | 1/2008 | Viola |
| 7,316,696 B2 | 1/2008 | Wilson, Jr. et al. |
| 7,322,995 B2 | 1/2008 | Buckman et al. |
| 7,326,223 B2 | 2/2008 | Wilson, Jr. |
| 7,329,266 B2 | 2/2008 | Royse et al. |
| 7,331,968 B2 | 2/2008 | Arp et al. |
| 7,338,503 B2 | 3/2008 | Rosenberg et al. |
| 7,357,805 B2 | 4/2008 | Masuda et al. |
| 7,367,939 B2 | 5/2008 | Smith et al. |
| 7,407,074 B2 | 8/2008 | Ortiz et al. |
| 7,419,495 B2 | 9/2008 | Menn et al. |
| 7,422,137 B2 | 9/2008 | Manzo |
| 7,431,724 B2 | 10/2008 | Manetakis et al. |
| 7,452,327 B2 | 11/2008 | Durgin et al. |

(56) References Cited

U.S. PATENT DOCUMENTS

| | | |
|---|---|---|
| 7,485,124 B2 | 2/2009 | Kuhns et al. |
| 7,488,335 B2 | 2/2009 | Sgro |
| 7,510,562 B2 | 3/2009 | Lindsay |
| 7,552,853 B2 | 6/2009 | Mas et al. |
| 7,559,937 B2 | 7/2009 | de la Torre et al. |
| 7,572,266 B2 | 8/2009 | Young et al. |
| 7,578,827 B2 | 8/2009 | Gadberry et al. |
| 7,582,095 B2 | 9/2009 | Shipp et al. |
| 7,585,304 B2 | 9/2009 | Hughett |
| 7,615,058 B2 | 11/2009 | Sixto, Jr. et al. |
| 7,615,060 B2 | 11/2009 | Stokes et al. |
| 7,621,926 B2 | 11/2009 | Wixey et al. |
| 7,637,917 B2 | 12/2009 | Whitfield et al. |
| 7,644,848 B2 | 1/2010 | Swayze et al. |
| 7,686,820 B2 | 3/2010 | Huitema et al. |
| 7,695,482 B2 | 4/2010 | Viola |
| 7,717,926 B2 | 5/2010 | Whitfield et al. |
| 7,727,247 B2 | 6/2010 | Kimura et al. |
| 7,727,248 B2 | 6/2010 | Smith et al. |
| 7,731,724 B2 | 6/2010 | Huitema et al. |
| 7,731,725 B2 | 6/2010 | Gadberry et al. |
| 7,736,388 B2 | 6/2010 | Goldfarb et al. |
| 7,740,639 B2 | 6/2010 | Hummel et al. |
| 7,740,641 B2 | 6/2010 | Huitema |
| 7,744,623 B2 | 6/2010 | Anderson |
| 7,752,853 B2 | 7/2010 | Singh et al. |
| 7,753,250 B2 | 7/2010 | Clauson et al. |
| 7,766,207 B2 | 8/2010 | Mather et al. |
| 7,766,925 B2 | 8/2010 | Stokes et al. |
| 7,770,773 B2 | 8/2010 | Whitman et al. |
| 7,776,058 B2 | 8/2010 | Rosenberg et al. |
| 7,780,688 B2 | 8/2010 | Sakakine et al. |
| 7,793,813 B2 | 9/2010 | Bettuchi |
| 7,806,903 B2 | 10/2010 | Shibata et al. |
| 7,819,886 B2 | 10/2010 | Whitfield et al. |
| 7,823,592 B2 | 11/2010 | Bettuchi et al. |
| 7,857,828 B2 | 12/2010 | Jabba et al. |
| 7,871,416 B2 | 1/2011 | Phillips |
| 7,875,029 B1 | 1/2011 | Hausen |
| 7,887,553 B2 | 2/2011 | Lehman et al. |
| 7,887,554 B2 | 2/2011 | Stokes et al. |
| 7,892,244 B2 | 2/2011 | Monassevitch et al. |
| 7,896,895 B2 | 3/2011 | Boudreaux et al. |
| 7,901,420 B2 | 3/2011 | Dunn |
| 7,905,890 B2 | 3/2011 | Whitfield et al. |
| 7,914,544 B2 | 3/2011 | Nguyen et al. |
| 7,914,551 B2 | 3/2011 | Ortiz et al. |
| 7,942,890 B2 | 5/2011 | D'Agostino et al. |
| 7,947,052 B2 | 5/2011 | Baxter, III et al. |
| 7,954,682 B2 | 6/2011 | Giordano et al. |
| 7,963,433 B2 | 6/2011 | Whitman et al. |
| 7,967,831 B2 | 6/2011 | Rosenberg et al. |
| 7,988,027 B2 | 8/2011 | Olson et al. |
| 7,998,155 B2 | 8/2011 | Manzo |
| 8,011,550 B2 | 9/2011 | Aranyi et al. |
| 8,011,555 B2 | 9/2011 | Tarinelli et al. |
| 8,016,178 B2 | 9/2011 | Olson et al. |
| 8,021,375 B2 | 9/2011 | Aldrich et al. |
| 8,021,378 B2 | 9/2011 | Sixto, Jr. et al. |
| 8,038,686 B2 | 10/2011 | Huitema et al. |
| 8,048,088 B2 | 11/2011 | Green et al. |
| 8,056,565 B2 | 11/2011 | Zergiebel |
| 8,062,310 B2 | 11/2011 | Shibata et al. |
| 8,062,311 B2 | 11/2011 | Litscher et al. |
| 8,062,314 B2 | 11/2011 | Sixto, Jr. et al. |
| 8,066,720 B2 | 11/2011 | Knodel et al. |
| 8,066,721 B2 | 11/2011 | Kortenbach et al. |
| 8,066,722 B2 | 11/2011 | Miyagi et al. |
| 8,070,760 B2 | 12/2011 | Fujita |
| 8,074,857 B2 | 12/2011 | Peterson et al. |
| 8,075,571 B2 | 12/2011 | Vitali et al. |
| 8,080,021 B2 | 12/2011 | Griego |
| 8,083,668 B2 | 12/2011 | Durgin et al. |
| 8,088,061 B2 | 1/2012 | Wells et al. |
| 8,091,755 B2 | 1/2012 | Kayan et al. |
| 8,100,926 B1 | 1/2012 | Filshie et al. |
| 8,128,643 B2 | 3/2012 | Aranyi et al. |
| 8,133,240 B2 | 3/2012 | Damarati |
| 8,137,368 B2 | 3/2012 | Kayan et al. |
| 8,142,451 B2 | 3/2012 | Boulnois et al. |
| 8,157,145 B2 | 4/2012 | Shelton, IV et al. |
| 8,157,149 B2 | 4/2012 | Olson et al. |
| 8,157,151 B2 | 4/2012 | Ingmanson et al. |
| 8,172,859 B2 | 5/2012 | Matsuno et al. |
| 8,172,870 B2 | 5/2012 | Shipp |
| 8,177,797 B2 | 5/2012 | Shimoji et al. |
| 8,182,529 B2 | 5/2012 | Gordon et al. |
| 8,187,290 B2 | 5/2012 | Buckman et al. |
| 8,192,449 B2 | 6/2012 | Maier et al. |
| 8,211,119 B2 | 7/2012 | Palmer et al. |
| 8,211,120 B2 | 7/2012 | Itoh |
| 8,211,124 B2 | 7/2012 | Ainsworth et al. |
| 8,216,255 B2 | 7/2012 | Smith et al. |
| 8,216,257 B2 | 7/2012 | Huitema et al. |
| 8,236,012 B2 | 8/2012 | Molitor et al. |
| 8,241,322 B2 | 8/2012 | Whitman et al. |
| 8,246,634 B2 | 8/2012 | Huitema et al. |
| 8,246,635 B2 | 8/2012 | Huitema |
| 8,262,678 B2 | 9/2012 | Matsuoka et al. |
| 8,262,679 B2 | 9/2012 | Nguyen |
| 8,267,944 B2 | 9/2012 | Sorrentino et al. |
| 8,267,945 B2 | 9/2012 | Nguyen et al. |
| 8,267,946 B2 | 9/2012 | Whitfield et al. |
| 8,272,554 B2 | 9/2012 | Whitman et al. |
| 8,282,655 B2 | 10/2012 | Whitfield et al. |
| 8,287,559 B2 | 10/2012 | Barker et al. |
| 8,308,743 B2 | 11/2012 | Matsuno et al. |
| 8,313,497 B2 | 11/2012 | Walberg et al. |
| 8,328,822 B2 | 12/2012 | Huitema et al. |
| 8,336,556 B2 | 12/2012 | Zergiebel |
| 8,348,130 B2 | 1/2013 | Shah et al. |
| 8,357,171 B2 | 1/2013 | Whitfield et al. |
| 8,366,709 B2 | 2/2013 | Schechter et al. |
| 8,366,726 B2 | 2/2013 | Dennis |
| 8,371,491 B2 | 2/2013 | Huitema et al. |
| 8,372,095 B2 | 2/2013 | Viola |
| 8,382,773 B2 | 2/2013 | Whitfield et al. |
| 8,398,655 B2 | 3/2013 | Cheng et al. |
| 8,403,138 B2 | 3/2013 | Weisshaupt et al. |
| 8,403,945 B2 | 3/2013 | Whitfield et al. |
| 8,403,946 B2 | 3/2013 | Whitfield et al. |
| 8,408,442 B2 | 4/2013 | Racenet et al. |
| 8,409,222 B2 | 4/2013 | Whitfield et al. |
| 8,409,223 B2 | 4/2013 | Sorrentino et al. |
| 8,419,752 B2 | 4/2013 | Sorrentino et al. |
| 8,430,892 B2 | 4/2013 | Bindra et al. |
| 8,444,660 B2 | 5/2013 | Adams et al. |
| 8,465,460 B2 | 6/2013 | Yodfat et al. |
| 8,465,502 B2 | 6/2013 | Zergiebel |
| 8,475,473 B2 | 7/2013 | Vandenbroek et al. |
| 8,480,688 B2 | 7/2013 | Boulnois et al. |
| 8,486,091 B2 | 7/2013 | Sorrentino et al. |
| 8,491,608 B2 | 7/2013 | Sorrentino et al. |
| 8,496,673 B2 | 7/2013 | Nguyen et al. |
| 8,506,580 B2 | 8/2013 | Zergiebel et al. |
| 8,512,357 B2 | 8/2013 | Viola |
| 8,518,055 B1 | 8/2013 | Cardinale et al. |
| 8,523,882 B2 | 9/2013 | Huitema et al. |
| 8,529,585 B2 | 9/2013 | Jacobs et al. |
| 8,529,586 B2 | 9/2013 | Rosenberg et al. |
| 8,529,588 B2 | 9/2013 | Ahlberg et al. |
| 8,545,486 B2 | 10/2013 | Malkowski |
| 8,545,519 B2 | 10/2013 | Aguirre et al. |
| 8,556,920 B2 | 10/2013 | Huitema et al. |
| 8,568,430 B2 | 10/2013 | Shipp |
| 8,579,918 B2 | 11/2013 | Whitfield et al. |
| 8,585,716 B2 | 11/2013 | Roskopf et al. |
| 8,585,717 B2 | 11/2013 | Sorrentino et al. |
| 8,603,109 B2 | 12/2013 | Aranyi et al. |
| 8,623,044 B2 | 1/2014 | Timm et al. |
| 8,628,547 B2 | 1/2014 | Weller et al. |
| 8,632,520 B2 | 1/2014 | Otley |
| 8,636,191 B2 | 1/2014 | Meagher |
| 8,652,151 B2 | 2/2014 | Lehman et al. |

(56) References Cited

U.S. PATENT DOCUMENTS

| | | |
|---|---|---|
| 8,652,152 B2 | 2/2014 | Aranyi et al. |
| 8,663,247 B2 | 3/2014 | Menn et al. |
| 8,685,048 B2 | 4/2014 | Adams et al. |
| 8,690,899 B2 | 4/2014 | Kogiso et al. |
| 8,708,210 B2 | 4/2014 | Zemlok et al. |
| 8,708,213 B2 | 4/2014 | Shelton, IV et al. |
| 8,709,027 B2 | 4/2014 | Adams et al. |
| 8,715,299 B2 | 5/2014 | Menn et al. |
| 8,720,766 B2 | 5/2014 | Hess et al. |
| 8,734,469 B2 | 5/2014 | Pribanic et al. |
| 8,747,423 B2 | 6/2014 | Whitfield et al. |
| 8,753,356 B2 | 6/2014 | Vitali et al. |
| 8,758,392 B2 | 6/2014 | Crainich |
| 8,771,169 B2 | 7/2014 | Whitman et al. |
| 8,795,302 B2 | 8/2014 | Wild |
| 8,808,310 B2 | 8/2014 | Jones et al. |
| 8,814,884 B2 | 8/2014 | Whitfield et al. |
| 8,821,516 B2 | 9/2014 | Huitema |
| 8,828,023 B2 | 9/2014 | Neff et al. |
| 8,839,954 B2 | 9/2014 | Disch |
| 8,845,659 B2 | 9/2014 | Whitfield et al. |
| 8,894,665 B2 | 11/2014 | Sorrentino et al. |
| 8,894,666 B2 | 11/2014 | Schulz et al. |
| 8,900,253 B2 | 12/2014 | Aranyi et al. |
| 8,915,930 B2 | 12/2014 | Huitema et al. |
| 8,915,931 B2 | 12/2014 | Boudreaux et al. |
| 8,939,974 B2 | 1/2015 | Boudreaux et al. |
| 8,945,151 B2 | 2/2015 | Salas |
| 8,950,646 B2 | 2/2015 | Viola |
| 8,968,337 B2 | 3/2015 | Whitfield et al. |
| 8,968,342 B2 | 3/2015 | Wingardner, III et al. |
| 8,973,804 B2 | 3/2015 | Hess et al. |
| 8,986,343 B2 | 3/2015 | Bourque et al. |
| 8,998,935 B2 | 4/2015 | Hart |
| 9,011,464 B2 | 4/2015 | Zammataro |
| 9,011,465 B2 | 4/2015 | Whitfield et al. |
| 9,028,511 B2 | 5/2015 | Weller et al. |
| 9,060,779 B2 | 6/2015 | Martinez |
| 9,084,604 B2 | 7/2015 | Litscher et al. |
| 9,089,334 B2 | 7/2015 | Sorrentino et al. |
| 9,113,892 B2 | 8/2015 | Malkowski et al. |
| 9,113,893 B2 | 8/2015 | Sorrentino et al. |
| 9,119,629 B2 | 9/2015 | Cardinale et al. |
| 9,186,136 B2 | 11/2015 | Malkowski et al. |
| 9,186,153 B2 | 11/2015 | Zammataro |
| 9,208,429 B2 | 12/2015 | Thornton et al. |
| 9,220,507 B1 | 12/2015 | Patel et al. |
| 9,226,825 B2 | 1/2016 | Starksen et al. |
| 9,232,947 B2 | 1/2016 | Brenner et al. |
| 9,265,486 B2 | 2/2016 | Hughett, Sr. et al. |
| 9,271,737 B2 | 3/2016 | Castro et al. |
| 9,282,972 B1 | 3/2016 | Patel et al. |
| 9,282,973 B2 | 3/2016 | Hughett, Sr. et al. |
| 9,358,011 B2 | 6/2016 | Sorrentino et al. |
| 9,364,216 B2 | 6/2016 | Rockrohr et al. |
| 9,364,240 B2 | 6/2016 | Whitfield et al. |
| 9,370,400 B2 | 6/2016 | Parihar |
| 9,393,024 B2 | 7/2016 | Whitfield et al. |
| 9,408,610 B2 | 8/2016 | Hartoumbekis |
| 9,414,844 B2 | 8/2016 | Zergiebel et al. |
| 9,433,411 B2 | 9/2016 | Racenet et al. |
| 9,433,422 B2 | 9/2016 | Crainich et al. |
| 9,439,654 B2 | 9/2016 | Sorrentino et al. |
| 9,445,810 B2 | 9/2016 | Cappola |
| 9,445,820 B2 | 9/2016 | Whiting |
| 9,456,824 B2 | 10/2016 | Willett et al. |
| 9,468,444 B2 | 10/2016 | Menn et al. |
| 9,480,477 B2 | 11/2016 | Aranyi et al. |
| 9,480,480 B2 | 11/2016 | Santilli et al. |
| 9,486,225 B2 | 11/2016 | Michler et al. |
| 9,498,227 B2 | 11/2016 | Zergiebel et al. |
| 9,504,472 B2 | 11/2016 | Kamler |
| 9,517,064 B2 | 12/2016 | Sarradon |
| 9,526,501 B2 | 12/2016 | Malkowski |
| 9,526,565 B2 | 12/2016 | Strobl |
| 9,532,787 B2 | 1/2017 | Zammataro |
| 9,545,254 B2 | 1/2017 | Sorrentino et al. |
| 9,549,741 B2 | 1/2017 | Zergiebel |
| 9,561,038 B2 | 2/2017 | Shelton, IV et al. |
| 9,566,066 B2 | 2/2017 | Kasvikis |
| 9,597,089 B2 | 3/2017 | Menn |
| 9,642,627 B2 | 5/2017 | Zammataro |
| 9,681,877 B2 | 6/2017 | Blake, III et al. |
| 9,687,247 B2 | 6/2017 | Aranyi et al. |
| 9,700,324 B2 | 7/2017 | Mazzucco et al. |
| 9,717,504 B2 | 8/2017 | Huitema |
| 9,717,505 B2 | 8/2017 | Whitfield et al. |
| 9,724,163 B2 | 8/2017 | Orban |
| 9,737,310 B2 | 8/2017 | Whitfield et al. |
| 9,750,500 B2 | 9/2017 | Malkowski |
| 9,763,668 B2 | 9/2017 | Whitfield et al. |
| 9,763,669 B2 | 9/2017 | Griego |
| 9,775,623 B2 | 10/2017 | Zammataro et al. |
| 9,775,624 B2 | 10/2017 | Rockrohr et al. |
| 9,782,164 B2 | 10/2017 | Mumaw et al. |
| 9,782,181 B2 | 10/2017 | Vitali et al. |
| 9,808,257 B2 | 11/2017 | Armenteros et al. |
| 9,848,886 B2 | 12/2017 | Malkowski et al. |
| 9,855,043 B2 | 1/2018 | Malkowski |
| 9,883,866 B2 | 2/2018 | Roundy et al. |
| 9,931,124 B2 | 4/2018 | Gokharu |
| 9,968,361 B2 | 5/2018 | Aranyi et al. |
| 9,968,362 B2 | 5/2018 | Malkowski et al. |
| 10,004,502 B2 | 6/2018 | Malkowski et al. |
| 10,136,939 B2 | 11/2018 | Minnelli et al. |
| 10,159,484 B2 | 12/2018 | Sorrentino et al. |
| 10,159,491 B2 | 12/2018 | Gokharu |
| 10,159,492 B2 | 12/2018 | Zammataro |
| 10,166,027 B2 | 1/2019 | Aranyi et al. |
| 10,231,732 B1 | 3/2019 | Racenet et al. |
| 10,231,735 B2 | 3/2019 | Sorrentino et al. |
| 10,231,738 B2 | 3/2019 | Sorrentino et al. |
| 10,258,346 B2 | 4/2019 | Zergiebel et al. |
| 10,292,712 B2 | 5/2019 | Shankarsetty |
| 10,349,936 B2 | 7/2019 | Rockrohr et al. |
| 10,349,950 B2 | 7/2019 | Aranyi et al. |
| 10,357,250 B2 | 7/2019 | Zammataro |
| 10,363,045 B2 | 7/2019 | Whitfield et al. |
| 10,368,876 B2 | 8/2019 | Bhatnagar et al. |
| 10,390,831 B2 | 8/2019 | Holsten et al. |
| 10,426,489 B2 | 10/2019 | Baril |
| 2002/0123742 A1 | 9/2002 | Baxter et al. |
| 2003/0014060 A1 | 1/2003 | Wilson et al. |
| 2003/0114867 A1 | 6/2003 | Bolduc et al. |
| 2003/0208231 A1 | 11/2003 | Williamson et al. |
| 2003/0229360 A1 | 12/2003 | Gayton |
| 2004/0097970 A1 | 5/2004 | Hughett |
| 2004/0097971 A1 | 5/2004 | Hughett |
| 2004/0133215 A1 | 7/2004 | Baxter |
| 2004/0138681 A1 | 7/2004 | Pier |
| 2004/0167545 A1 | 8/2004 | Sadler et al. |
| 2004/0176783 A1 | 9/2004 | Edoga et al. |
| 2004/0176784 A1 | 9/2004 | Okada |
| 2004/0193213 A1 | 9/2004 | Aranyi et al. |
| 2004/0232197 A1 | 11/2004 | Shelton et al. |
| 2005/0010242 A1 | 1/2005 | Lindsay |
| 2005/0090837 A1 | 4/2005 | Sixto et al. |
| 2005/0096670 A1 | 5/2005 | Wellman et al. |
| 2005/0096671 A1 | 5/2005 | Wellman et al. |
| 2005/0107810 A1 | 5/2005 | Morales et al. |
| 2005/0107811 A1 | 5/2005 | Starksen et al. |
| 2005/0107871 A1 | 5/2005 | Realyvasquez et al. |
| 2005/0125010 A1 | 6/2005 | Smith et al. |
| 2005/0149068 A1 | 7/2005 | Williams et al. |
| 2005/0149069 A1 | 7/2005 | Bertolero et al. |
| 2005/0171560 A1 | 8/2005 | Hughett |
| 2005/0175703 A1 | 8/2005 | Hunter et al. |
| 2005/0177176 A1 | 8/2005 | Gerbi et al. |
| 2005/0216036 A1 | 9/2005 | Nakao |
| 2005/0216056 A1 | 9/2005 | Valdevit et al. |
| 2005/0222665 A1 | 10/2005 | Aranyi |
| 2005/0228416 A1 | 10/2005 | Burbank et al. |
| 2005/0256529 A1 | 11/2005 | Yawata et al. |
| 2005/0267495 A1 | 12/2005 | Ginn et al. |

(56) References Cited

U.S. PATENT DOCUMENTS

| | | |
|---|---|---|
| 2005/0273122 A1 | 12/2005 | Theroux et al. |
| 2005/0277956 A1 | 12/2005 | Francese et al. |
| 2005/0277958 A1 | 12/2005 | Levinson |
| 2005/0288689 A1 | 12/2005 | Kammerer et al. |
| 2006/0000867 A1 | 1/2006 | Shelton et al. |
| 2006/0004388 A1 | 1/2006 | Whayne et al. |
| 2006/0009789 A1 | 1/2006 | Gambale et al. |
| 2006/0009790 A1 | 1/2006 | Blake et al. |
| 2006/0009792 A1 | 1/2006 | Baker et al. |
| 2006/0020271 A1 | 1/2006 | Stewart et al. |
| 2006/0079115 A1 | 4/2006 | Aranyi |
| 2006/0085015 A1 | 4/2006 | Whitfield et al. |
| 2006/0085021 A1 | 4/2006 | Wenzler |
| 2006/0100649 A1 | 5/2006 | Hart |
| 2006/0124485 A1 | 6/2006 | Kennedy |
| 2006/0163312 A1 | 7/2006 | Viola et al. |
| 2006/0173470 A1 | 8/2006 | Oray et al. |
| 2006/0190013 A1 | 8/2006 | Menn |
| 2006/0217749 A1 | 9/2006 | Wilson et al. |
| 2006/0224165 A1 | 10/2006 | Surti et al. |
| 2006/0224170 A1 | 10/2006 | Duff |
| 2006/0235439 A1 | 10/2006 | Molitor et al. |
| 2006/0235493 A1 | 10/2006 | Shibata et al. |
| 2006/0241655 A1 | 10/2006 | Viola |
| 2006/0259045 A1 | 11/2006 | Damarati |
| 2006/0259049 A1 | 11/2006 | Harada et al. |
| 2007/0021766 A1 | 1/2007 | Belagali et al. |
| 2007/0038233 A1 | 2/2007 | Martinez et al. |
| 2007/0049947 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0083218 A1 | 4/2007 | Morris |
| 2007/0093790 A1 | 4/2007 | Downey et al. |
| 2007/0112365 A1 | 5/2007 | Hilal et al. |
| 2007/0118161 A1 | 5/2007 | Kennedy et al. |
| 2007/0118174 A1 | 5/2007 | Chu |
| 2007/0173866 A1 | 7/2007 | Sorrentino et al. |
| 2007/0185504 A1 | 8/2007 | Manetakis et al. |
| 2007/0191868 A1 | 8/2007 | Theroux et al. |
| 2007/0203510 A1 | 8/2007 | Bettuchi |
| 2007/0276417 A1 | 11/2007 | Mendes, Jr. et al. |
| 2007/0282355 A1 | 12/2007 | Brown et al. |
| 2007/0288039 A1 | 12/2007 | Aranyi et al. |
| 2007/0293875 A1 | 12/2007 | Soetikno et al. |
| 2008/0004636 A1 | 1/2008 | Walberg et al. |
| 2008/0045981 A1 | 2/2008 | Margolin et al. |
| 2008/0051808 A1 | 2/2008 | Rivera et al. |
| 2008/0103510 A1 | 5/2008 | Taylor et al. |
| 2008/0147092 A1 | 6/2008 | Rogge et al. |
| 2008/0167665 A1 | 7/2008 | Arp et al. |
| 2008/0228199 A1 | 9/2008 | Cropper et al. |
| 2008/0255413 A1 | 10/2008 | Zemlok et al. |
| 2008/0255589 A1 | 10/2008 | Blakeney et al. |
| 2008/0306492 A1 | 12/2008 | Shibata et al. |
| 2008/0306493 A1 | 12/2008 | Shibata et al. |
| 2008/0312670 A1 | 12/2008 | Lutze et al. |
| 2009/0088783 A1 | 4/2009 | Kennedy et al. |
| 2009/0182193 A1 | 7/2009 | Whitman et al. |
| 2009/0204115 A1 | 8/2009 | Dees, Jr. et al. |
| 2009/0209946 A1 | 8/2009 | Swayze et al. |
| 2009/0228023 A1 | 9/2009 | Cui |
| 2009/0261142 A1 | 10/2009 | Milliman et al. |
| 2009/0264904 A1 | 10/2009 | Aldrich et al. |
| 2009/0312775 A1 | 12/2009 | Gilkey et al. |
| 2009/0326558 A1 | 12/2009 | Cui et al. |
| 2010/0089970 A1 | 4/2010 | Smith et al. |
| 2010/0274264 A1 | 10/2010 | Schulz et al. |
| 2010/0318103 A1 | 12/2010 | Cheng et al. |
| 2010/0331862 A1 | 12/2010 | Monassevitch et al. |
| 2011/0054498 A1 | 3/2011 | Monassevitch et al. |
| 2011/0087220 A1 | 4/2011 | Felder et al. |
| 2011/0087268 A1 | 4/2011 | Livneh |
| 2011/0144662 A1 | 6/2011 | McLawhorn et al. |
| 2011/0208211 A1 | 8/2011 | Whitfield et al. |
| 2011/0208212 A1 | 8/2011 | Zergiebel et al. |
| 2011/0218554 A1 | 9/2011 | Cheng et al. |
| 2011/0224700 A1 | 9/2011 | Schmidt et al. |
| 2011/0295290 A1 | 12/2011 | Whitfield |
| 2011/0313437 A1 | 12/2011 | Yeh |
| 2012/0022526 A1 | 1/2012 | Aldridge et al. |
| 2012/0046671 A1 | 2/2012 | Matsuoka et al. |
| 2012/0048759 A1 | 3/2012 | Disch et al. |
| 2012/0053402 A1 | 3/2012 | Conlon et al. |
| 2012/0226291 A1 | 9/2012 | Malizia et al. |
| 2012/0253298 A1 | 10/2012 | Henderson et al. |
| 2012/0265220 A1 | 10/2012 | Menn |
| 2012/0330326 A1 | 12/2012 | Creston et al. |
| 2013/0041379 A1 | 2/2013 | Bodor et al. |
| 2013/0131697 A1 | 5/2013 | Hartoumbekis |
| 2013/0165951 A1 | 6/2013 | Blake, III |
| 2013/0172909 A1 | 7/2013 | Harris |
| 2013/0172910 A1 | 7/2013 | Malkowski |
| 2013/0172911 A1* | 7/2013 | Rockrohr ............... A61B 90/08 606/143 |
| 2013/0175320 A1 | 7/2013 | Mandakolathur Vasudevan et al. |
| 2013/0226200 A1 | 8/2013 | Kappel et al. |
| 2013/0253540 A1 | 9/2013 | Castro et al. |
| 2013/0325057 A1 | 12/2013 | Larson et al. |
| 2014/0074143 A1 | 3/2014 | Fitzgerald et al. |
| 2014/0188159 A1 | 7/2014 | Steege |
| 2014/0263565 A1 | 9/2014 | Lytle, IV et al. |
| 2014/0276970 A1 | 9/2014 | Messerly et al. |
| 2014/0371728 A1 | 12/2014 | Vaughn |
| 2015/0032131 A1 | 1/2015 | Sorrentino et al. |
| 2015/0201953 A1 | 7/2015 | Strobl et al. |
| 2015/0265282 A1 | 9/2015 | Miles et al. |
| 2015/0313452 A1 | 11/2015 | Nasser et al. |
| 2015/0314451 A1 | 11/2015 | Nixon |
| 2016/0004956 A1 | 1/2016 | Reynolds et al. |
| 2016/0030044 A1 | 2/2016 | Zammataro |
| 2016/0113655 A1 | 4/2016 | Holsten |
| 2016/0151071 A1 | 6/2016 | Tokarz et al. |
| 2016/0213377 A1 | 7/2016 | Shankarsetty |
| 2016/0242767 A1 | 8/2016 | Kasvikis |
| 2016/0242789 A1 | 8/2016 | Sorrentino et al. |
| 2016/0256157 A1 | 9/2016 | Rockrohr et al. |
| 2016/0256158 A1 | 9/2016 | Whitfield et al. |
| 2016/0262764 A1 | 9/2016 | Gokharu |
| 2016/0296236 A1 | 10/2016 | Whitfield et al. |
| 2016/0338695 A1 | 11/2016 | Hartoumbekis |
| 2016/0338699 A1 | 11/2016 | Sorrentino et al. |
| 2017/0027581 A1 | 2/2017 | Zergiebel et al. |
| 2017/0049449 A1 | 2/2017 | Aranyi et al. |
| 2017/0065277 A1 | 3/2017 | Malkowski |
| 2017/0065281 A1 | 3/2017 | Zammataro |
| 2017/0086846 A1 | 3/2017 | Sorrentino et al. |
| 2017/0086850 A1 | 3/2017 | Zergiebel |
| 2017/0128071 A1 | 5/2017 | Holsten et al. |
| 2017/0172780 A1 | 6/2017 | Murthy Aravalli |
| 2017/0202567 A1 | 7/2017 | Griffiths et al. |
| 2017/0238936 A1 | 8/2017 | Mujawar |
| 2017/0245921 A1 | 8/2017 | Joseph et al. |
| 2017/0252042 A1 | 9/2017 | Kethman et al. |
| 2017/0258472 A1 | 9/2017 | Aranyi et al. |
| 2017/0290587 A1 | 10/2017 | Schober et al. |
| 2017/0325814 A1 | 11/2017 | Malkowski |
| 2017/0340325 A1 | 11/2017 | Baril et al. |
| 2017/0340331 A1 | 11/2017 | Hu et al. |
| 2017/0340332 A1 | 11/2017 | Whitfield et al. |
| 2017/0360449 A1 | 12/2017 | Rockrohr et al. |
| 2018/0008276 A1 | 1/2018 | Bhatnagar et al. |
| 2018/0008277 A1 | 1/2018 | Baril |
| 2018/0021041 A1 | 1/2018 | Zhang et al. |
| 2018/0070952 A1 | 3/2018 | Malkowski et al. |
| 2018/0116671 A1 | 5/2018 | Prior |
| 2018/0116673 A1 | 5/2018 | Baril et al. |
| 2018/0116674 A1 | 5/2018 | Baril |
| 2018/0116675 A1 | 5/2018 | Baril |
| 2018/0116676 A1 | 5/2018 | Williams |
| 2018/0168660 A1 | 6/2018 | Gokharu |
| 2018/0214156 A1 | 8/2018 | Baril et al. |
| 2018/0221028 A1 | 8/2018 | Williams |
| 2018/0228492 A1 | 8/2018 | Aranyi et al. |
| 2018/0228567 A1 | 8/2018 | Baril et al. |

(56) References Cited

U.S. PATENT DOCUMENTS

| | | | |
|---|---|---|---|
| 2018/0235632 A1 | 8/2018 | Mujawar et al. |
| 2018/0235633 A1 | 8/2018 | Baril et al. |
| 2018/0235637 A1 | 8/2018 | Xu et al. |
| 2018/0242977 A1 | 8/2018 | Tan et al. |
| 2018/0263624 A1 | 9/2018 | Malkowski et al. |
| 2018/0271526 A1 | 9/2018 | Zammataro |
| 2018/0317927 A1 | 11/2018 | Cai et al. |
| 2018/0317928 A1 | 11/2018 | P V R |
| 2018/0325519 A1 | 11/2018 | Baril et al. |
| 2019/0000449 A1 | 1/2019 | Baril et al. |
| 2019/0000482 A1 | 1/2019 | Hu et al. |
| 2019/0000584 A1 | 1/2019 | Baril |
| 2019/0021738 A1 | 1/2019 | Hartoumbekis |
| 2019/0038375 A1 | 2/2019 | Baril et al. |
| 2019/0046202 A1 | 2/2019 | Baril et al. |
| 2019/0046203 A1 | 2/2019 | Baril et al. |
| 2019/0046207 A1 | 2/2019 | Czernik et al. |
| 2019/0046208 A1 | 2/2019 | Baril et al. |
| 2019/0053806 A1 | 2/2019 | Zhang et al. |
| 2019/0053808 A1 | 2/2019 | Baril et al. |
| 2019/0059904 A1 | 2/2019 | Zammataro |
| 2019/0076147 A1 | 3/2019 | Baril et al. |
| 2019/0076148 A1 | 3/2019 | Baril et al. |
| 2019/0076149 A1 | 3/2019 | Baril et al. |
| 2019/0076150 A1 | 3/2019 | Gokharu |
| 2019/0076210 A1 | 3/2019 | Baril et al. |
| 2019/0133583 A1 | 5/2019 | Baril et al. |
| 2019/0133584 A1 | 5/2019 | Baril et al. |
| 2019/0133593 A1 | 5/2019 | P V R |
| 2019/0133594 A1 | 5/2019 | Dinino et al. |
| 2019/0133595 A1 | 5/2019 | Baril et al. |
| 2019/0150935 A1 | 5/2019 | Raikar et al. |
| 2019/0175176 A1 | 6/2019 | Zammataro |
| 2019/0175187 A1 | 6/2019 | P V R |
| 2019/0175188 A1 | 6/2019 | P V R |
| 2019/0175189 A1 | 6/2019 | P V R |
| 2019/0192139 A1 | 6/2019 | Rockrohr et al. |
| 2019/0209177 A1 | 7/2019 | Whitfield et al. |
| 2019/0216464 A1 | 7/2019 | Baril et al. |
| 2019/0239893 A1 | 8/2019 | Shankarsetty |

FOREIGN PATENT DOCUMENTS

| | | |
|---|---|---|
| CN | 103251441 A | 8/2013 |
| CN | 104605911 B | 2/2017 |
| DE | 2005001664 U1 | 5/2005 |
| DE | 202007003398 U1 | 6/2007 |
| DE | 202009006113 U1 | 7/2009 |
| EP | 0000756 A1 | 2/1979 |
| EP | 0406724 A1 | 1/1991 |
| EP | 0514139 A2 | 11/1992 |
| EP | 0732078 A2 | 9/1996 |
| EP | 1769757 A1 | 4/2007 |
| EP | 3132756 A1 | 2/2017 |
| GB | 2073022 A | 10/1981 |
| JP | 2003033361 A | 2/2003 |
| JP | 2006154230 A | 6/2006 |
| JP | 2006277221 A | 10/2006 |
| JP | 2008017876 A | 1/2008 |
| JP | 2011186812 A | 9/2011 |
| JP | 2013166982 A | 8/2013 |
| WO | 9003763 A1 | 4/1990 |
| WO | 0042922 A1 | 7/2000 |
| WO | 0166001 A2 | 9/2001 |
| WO | 0167965 A1 | 9/2001 |
| WO | 2016192096 A1 | 12/2016 |
| WO | 2016192718 A2 | 12/2016 |
| WO | 2016197350 A1 | 12/2016 |
| WO | 2016206015 A1 | 12/2016 |
| WO | 2017084000 A1 | 5/2017 |
| WO | 2017146138 A1 | 8/2017 |

OTHER PUBLICATIONS

Extended European Search Report corresponding to European Appln. No. EP 17 17 3508.7 dated Sep. 29, 2017.
Chinese Second Office Action corresponding to Chinese Appln. No. CN 201410076318.8 dated Oct. 10, 2017.
Extended European Search Report corresponding to European Appln. No. EP 17 18 0570.8 dated Dec. 6, 2017.
European Office Action corresponding to EP 12 152 989.5 dated May 4, 2015.
Australian Office Action corresponding to AU 2009212759 dated May 7, 2015.
Chinese Office Action corresponding to Int'l Appln No. CN 201210212642.9 dated Jun. 3, 2015.
European Office Action corresponding to Int'l Appln No. EP 04 719 757.9 dated Jun. 12, 2015.
European Office Action corresponding to Int'l Appln No. EP 13 166 382.5 dated Jun. 19, 2015.
Japanese Office Action corresponding to Int'l Application No. JP 2010-226908 dated Jun. 26, 2015.
Extended European Search Report corresponding to Int'l Application No. EP 15 15 5024.1 dated Jul. 17, 2015.
Extended European Search Report corresponding to Int'l Application No. EP 14 19 2026.4 dated Jul. 17, 2015.
Japanese Office Action corresponding to Int'l Application No. JP 2011-160126 dated Aug. 10, 2015.
Extended European Search Report corresponding to Int'l Application No. EP 14 15 0321.9 dated Sep. 23, 2015.
Extended European Search Report corresponding to Int'l Application No. EP 11 25 0675.3 dated Oct. 7, 2015.
Extended European Search Report corresponding to Int'l Application No. EP 11 25 0674.6 dated Oct. 7, 2015.
Extended European Search Report corresponding to Int'l Application No. EP 12 19 3447.5 dated Oct. 19, 2015.
Canadian Office Action corresponding to Int'l Application No. CA 2,675,875 dated Oct. 26, 2015.
Japanese Office Action corresponding to Int'l Application No. JP 2015-005629 dated Oct. 28, 2015.
Japanese Office Action corresponding to Int'l Application No. JP 2014-245081 dated Oct. 28, 2015.
Canadian Office Action corresponding to Int'l Application No. CA 2,675,921 dated Oct. 30, 2015.
Chinese Office Action corresponding to Int'l Application No. CN 201210555570.8 dated Nov. 2, 2015.
Canadian Office Action corresponding to Int'l Application No. CA 2,676,309 dated Nov. 3, 2015.
Canadian Office Action corresponding to Int'l Application No. CA 2,676,211 dated Nov. 24, 2015.
Canadian Office Action corresponding to Int'l Application No. CA 2,676,547 dated Nov. 25, 2015.
Extended European Search Report corresponding to Int'l Application No. EP 15 17 3809.3 dated Nov. 25, 2015.
Chinese Office Action corresponding to Int'l Application No. CN 201210586814.9 dated Dec. 2, 2015.
Extended European Search Report corresponding to Int'l Application No. EP 12 17 2940.4 dated Dec. 14, 2015.
Chinese First Office Action corresponding to Int'l Appln. No. CN 201210586826.1 dated Dec. 30, 2015.
Extended European Search Report corresponding to Int'l Appln. No. EP 15 18 5362.9 dated Feb. 12, 2016.
Extended European Search Report corresponding to Int'l Appln. No. EP 12 19 7813.4 dated Mar. 7, 2016.
Canadian Office Action corresponding to Int'l Appln. No. CA 2,676,465 dated Mar. 8, 2016.
Japanese Office Action corresponding to Int'l Appln. No. JP 2014-245081 dated Mar. 18, 2016.
Japanese Office Action corresponding to Int'l Appln. No. JP 2015-005629 dated Mar. 18, 2016.
Extended European Search Report corresponding to Int'l Appln. No. EP 15 19 3549.1 dated Mar. 22, 2016.
International Search Report and Written Opinion corresponding to Int'l Appln. No. PCT/CN2015/082199 dated Mar. 31, 2016.
Extended European Search Report corresponding to Int'l Appln. No. EP 15 19 7251.0 dated Apr. 8, 2016.

(56) References Cited

OTHER PUBLICATIONS

Extended European Search Report corresponding to Int'l Appln. No. EP 16 15 0739.7 dated May 17, 2016.
Canadian Office Action corresponding to Int'l Appln. No. CA 2,716,672 dated May 31, 2016.
Canadian Office Action corresponding to Int'l Appln. No. CA 2,717,448 dated May 31, 2016.
Canadian Office Action corresponding to In'l Appln. No. CA 2,721,951 dated Jun. 1, 2016.
Partial European Search Report corresponding to Int'l Appln. No. EP 16 15 0287.7 dated Jun. 16, 2016.
Chinese Second Office Action corresponding to Int'l Appln. No. CN 201210555570.8 dated Jun. 20, 2016.
Chinese First Office Action corresponding to Chinese Appln. No. CN 201410076318.8 dated Jan. 23, 2017.
Extended European Search Report corresponding to European Appln. No. EP 16 18 3184.7 dated Jan. 24, 2017.
Japanese Office Action corresponding to Japanese Appln. No. JP 2016-097807 dated Feb. 14, 2017.
European Office Action corresponding to European Appln. No. EP 12 19 34475 dated Apr. 4, 2017.
Chinese First Office Action corresponding to Chinese Appln. No. CN 201410008877.5 dated Apr. 6, 2017.
Extended European Search Report corresponding to European Appln. No. EP 17 15 3714.5 dated May 11, 2017.
Extended European Search Report corresponding to European Appln. No. EP 17 15 8519.3 dated May 19, 2017.
Extended European Search Report corresponding to European Appln. No. EP 17 15 7606.9 dated May 22, 2017.
European Office Action corresponding to European Appln. No. EP 11 25 0674.6 dated May 23, 2017.
Canadian Office Action corresponding to Canadian Appln. No. CA 2,743,402 dated May 30, 2017.
European Office Action corresponding to European Appln. No. EP 16 15 9324.9 dated Aug. 7, 2017.
The extended European Search Report corresponding to European Application No. EP 07 25 3905.9, completed Jan. 29, 2008; dated Feb. 7, 2008; (7 Pages).
International Search Report corresponding to International Application No. PCT-US08-58185, completed Sep. 4, 2008; dated Sep. 9, 2008; (2 Pages).
The International Search Report corresponding to International Application No. PCT-US08-59859, completed Sep. 14, 2008; dated Sep. 18, 2008; (2 Pages).
The extended European Search Report corresponding to European Application No. EP 07 25 3807.7, completed Nov. 7, 2008; dated Nov. 26, 2008; (11 Pages).
The extended European Search Report corresponding to European Application No. EP 09 25 2049.3, completed Dec. 11, 2009; dated Jan. 12, 2010; (3 Pages).
The extended European Search Report corresponding to European Application No. EP 09 25 2050.1, completed Dec. 23, 2009; dated Jan. 21, 2010; (3 Pages).
The extended European Search Report corresponding to European Application No. EP 09 25 2051.9, completed Dec. 21, 2009; dated Jan. 28, 2010; (3 Pages).
The extended European Search Report corresponding to European Application No. EP 09 25 2052.7, completed Nov. 16, 2009; dated Nov. 24, 2009; (3 Pages).
The extended European Search Report corresponding to European Application No. EP 09 25 2053.5, completed Nov. 24, 2009; dated Dec. 1, 2009; (3 Pages).
The extended European Search Report corresponding to European Application No. EP 09 25 2054.3, completed Jan. 7, 2010; dated Jan. 22, 2010; (3 Pages).
The extended European Search Report corresponding to European Application No. EP 09 25 2056.8, completed Jan. 8, 2010; dated Feb. 5, 2010; (3 Pages).
The extended European Search Report corresponding to European Application No. EP 10 25 0497.4, completed May 4, 2010; dated May 12, 2010; (6 Pages).
The extended European Search Report corresponding to European Application No. EP 10 25 2079.8, completed Mar. 8, 2011; dated Mar. 17, 2011; (3 Pages).
The European Search Report corresponding to European Application No. EP 05 81 0218.7, completed Apr. 18, 2011; dated May 20, 2011; (3 pages).
The European Search Report corresponding to European Application No. EP 05 80 7612.6, completed May 2, 2011; dated May 20, 2011; (3 pages).
The extended European Search Report corresponding to European Application No. EP 10 25 1737.2, completed May 9, 2011; dated May 20, 2011; (4 pages).
The extended European Search Report corresponding to European Application No. EP 11 25 0214.1, completed May 25, 2011; dated Jun. 1, 2011; (3 Pages).
The extended European Search Report corresponding to European Application No. EP 11 00 2681.2, completed May 31, 2011; dated Jun. 10, 2011; (3 Pages).
The European Search Report corresponding to European Application No. EP 05 80 2686.5, completed Jan. 9, 2012; dated Jan. 18, 2012; (3 Pages).
The extended European Search Report corresponding to European Application No. EP 12 15 1313.9, completed Mar. 20, 2012 and dated Apr. 12, 2012; (5 Pages).
The extended European Search Report corresponding to European Application No. EP 12 16 1291.5, completed Apr. 24, 2012 and dated May 4, 2012; (5 Pages).
The extended European Search Report corresponding to European Application No. EP 12 16 5891.8, completed Jun. 12, 2012 and dated Jun. 20, 2012; (6 Pages).
The extended European Search Report corresponding to European Application No. EP 12 16 2288.0, completed Jun. 4, 2012 and dated Jul. 7, 2012; (6 Pages).
The extended European Search Report corresponding to European Application No. EP 12 16 4955.2, completed Aug. 23, 2012 and dated Sep. 4, 2012; (5 Pages).
The extended European Search Report corresponding to European Application No. EP 11 25 0754.6, completed Oct. 22, 2012 and dated Oct. 31, 2012; (6 Pages).
The extended European Search Report corresponding to European Application No. EP 12 18 6401.1, completed Nov. 22, 2012 and dated Nov. 30, 2012; (7 Pages).
The extended European Search Report corresponding to European Application No. EP 12 18 6448.2, completed Nov. 28, 2012 and dated Dec. 10, 2012; (6 Pages).
The extended European Search Report corresponding to European Application No. EP 12 19 1706.6, completed Dec. 19, 2012 and dated Jan. 8, 2013; (6 Pages).
The Extended European Search Report corresponding to EP 12 19 8745.7, completed Mar. 19, 2013 and dated Apr. 11, 2013; (8 Pages).
The Extended European Search Report corresponding to EP 12 15 2989.5, completed Apr. 9, 2013 and dated Apr. 18, 2013; (9 Pages).
The Extended European Search Report corresponding to EP 08 73 2820.9, completed Jul. 2, 2013 and dated Jul. 9, 2013; (10 Pages).
The Extended European Search Report corresponding to EP 13 17 2008.8, completed Aug. 14, 2013 and dated Aug. 28, 2013; (8 Pages).
The Extended European Search Report corresponding to EP 13 16 6382.5, completed Nov. 19, 2013 and dated Nov. 28, 2013; (8 Pages).
The Extended European Search Report corresponding to EP 11 25 0194.5, completed Nov. 25, 2013 and dated Dec. 3, 2013; (8 Pages).
The Extended European Search Report corresponding to EP 10 25 1798.4, completed Dec. 12, 2013 and dated Jan. 2, 2014; (9 Pages).
"Salute II Disposable Fixation Device", Technique Guide—Laparoscopic and Open Inguinal and Ventral Hernia Repair; Davol, A Bard Company, 2006; (7 Pages).
The Extended European Search Report corresponding to EP 10 25 2112.7, completed Jul. 29, 2014 and dated Aug. 5, 2014; (8 pp).

(56) References Cited

OTHER PUBLICATIONS

The Extended European Search Report corresponding to EP 14 15 1673.2, completed Apr. 25, 2014 and dated May 8, 2014; (8 pp).
Japanese Office Action corresponding to JP 2011-160130 dated Dec. 1, 2014.
Chinese Office Action corresponding to CN 201210015011.8 dated Jan. 4, 2015.
Japanese Office Action corresponding to JP 2011-160126 dated Jan. 9, 2015.
Japanese Office Action corresponding to JP 2011-184521 dated Jan. 15, 2015.
Extended European Search Report corresponding to 14 18 2236.1 dated Jan. 20, 2015.
Chinese Office Action corresponding to CN 201110201736.1 dated Feb. 9, 2015.
Extended European Search Report corresponding to EP 14 16 1540.1 dated Feb. 27, 2015.
Australian Office Action corresponding to AU 2010226985 dated Mar. 31, 2015.
Australian Office Action corresponding to AU 2013211526 dated Apr. 6, 2015.
Australian Office Action corresponding to AU 2011211463 dated Apr. 13, 2015.
Australian Office Action corresponding to AU 2013254887 dated Apr. 14, 2015.
Japanese Office Action corresponding to JP 2013-225272 dated May 1, 2015.
Extended European Search Report corresponding to Patent Application EP 18154617.7 dated Jun. 25, 2018.
Extended European Search Report corresponding to Patent Application EP 18155158.1 dated Jun. 28, 2018.
Extended European Search Report corresponding to Patent Application EP 15877428.1 dated Jul. 2, 2018.
Extended European Search Report corresponding to Patent Application EP 18157789.1 dated Jul. 5, 2018.
Canadian Office Action corresponding to Patent Application CA 2,972,444 dated Aug. 9, 2018.
Extended European Search Report corresponding to Patent Application EP 18156458.4 dated Sep. 3, 2018.
Extended European Search Report corresponding to Patent Application EP 18171682.0 dated Sep. 18, 2018.
Extended European Search Report corresponding to Patent Application EP 15878354.8 dated Sep. 19, 2018.
Extended European Search Report corresponding to Patent Application EP 18183394.8 dated Sep. 28, 2018.
Extended European Search Report corresponding to Patent Application EP 18163041.9 dated Sep. 28, 2018.
Extended European Search Report corresponding to Patent Application EP 18170524.5 dated Oct. 1, 2018.
Japanese Office Action corresponding to Patent Application JP 2017-536546 dated Oct. 15, 2018.
Extended European Search Report corresponding to Patent Application EP 18187640.0 dated Nov. 30, 2018.
Extended European Search Report corresponding to Patent Application EP 18187690.5 dated Nov. 30, 2018.
Chinese First Office Action corresponding to Patent Application CN 201510696298.9 dated Dec. 3, 2018.
Extended European Search Report corresponding to Patent Application EP 18158143.0 dated Dec. 5, 2018.
International Search Report corresponding to Int'l Patent Appln. PCT/US2018/050316 dated Dec. 31, 2018.
International Search Report corresponding to Int'l Patent Appln. PCT/US2018/050336 dated Jan. 7, 2019.
International Search Report corresponding to Int'l Patent Appln. PCT/US2018/050325 dated Jan. 7, 2019.
International Search Report corresponding to Int'l Patent Appln. PCT/US2018/045306 dated Jan. 16, 2019.
International Search Report corresponding to Int'l Patent Appln. PCT/US2018/050349 dated Jan. 21, 2019.
International Search Report corresponding to Int'l Patent Appln. PCT/US2018/045725 dated Jan. 28, 2019.
Extended European Search Report corresponding to European Patent Application EP 18208630.6 dated Feb. 12, 2019.
International Search Report corresponding to Int'l Patent Appln. PCT/US2018/057910 dated Feb. 22, 2019.
International Search Report corresponding to Int'l Patent Appln. PCT/US2018/057922 dated Feb. 22, 2019.
International Search Report corresponding to Int'l Patent Appln. PCT/US2018/058078 dated Feb. 22, 2019.
International Search Report corresponding to Int'l Patent Appln. PCT/US2018/058603 dated Feb. 22, 2019.
International Search Report corresponding to Int'l Patent Appln. PCT/US2018/057221 dated Mar. 11, 2019.
Extended European Search Report corresponding to European Patent Application EP 18212043.6 dated Apr. 24, 2019.
Extended European Search Report corresponding to European Patent Application EP 18211565.9 dated Apr. 26, 2019.
Extended European Search Report corresponding to European Patent Application EP 18211921.4 dated Apr. 30, 2019.
Chinese First Office Action corresponding to Chinese Patent Application CN 201510868226.8 dated May 29, 2019.
Extended European Search Report corresponding to European Patent Application EP 15905685.2 dated May 29, 2019.
European Office Action corresponding to European Patent Application EP 17157606.9 dated Jul. 2, 2019.
Extended European Search Report corresponding to European Patent Application EP 15908025.8 dated Jul. 2, 2019.
Partial Supplementary European Search Report corresponding to European Patent Application EP 16884297.9 dated Jul. 30, 2019.
Extended European Search Report dated Jul. 3, 2019 corresponding to counterpart Patent Application EP 18212054.3.

* cited by examiner

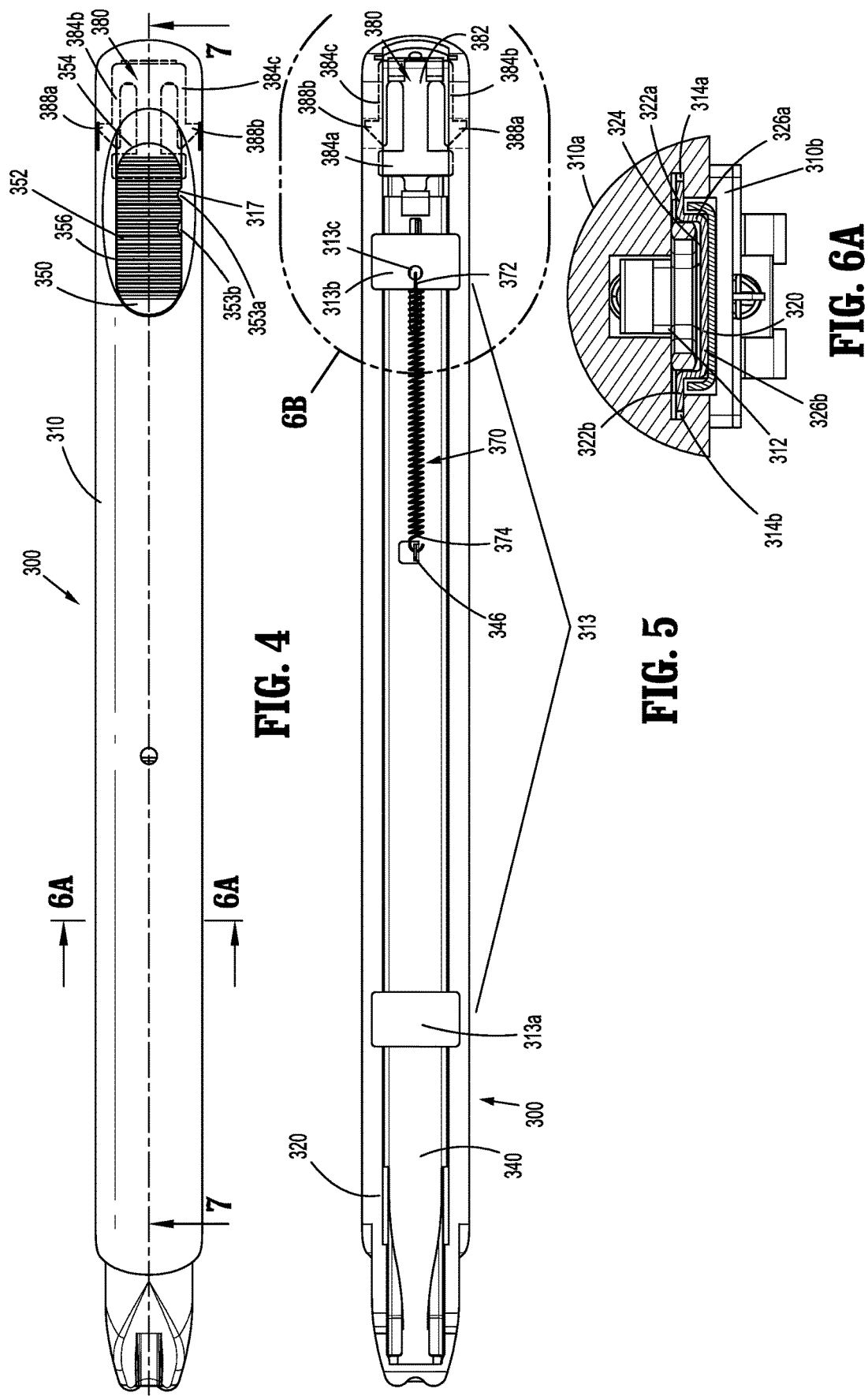

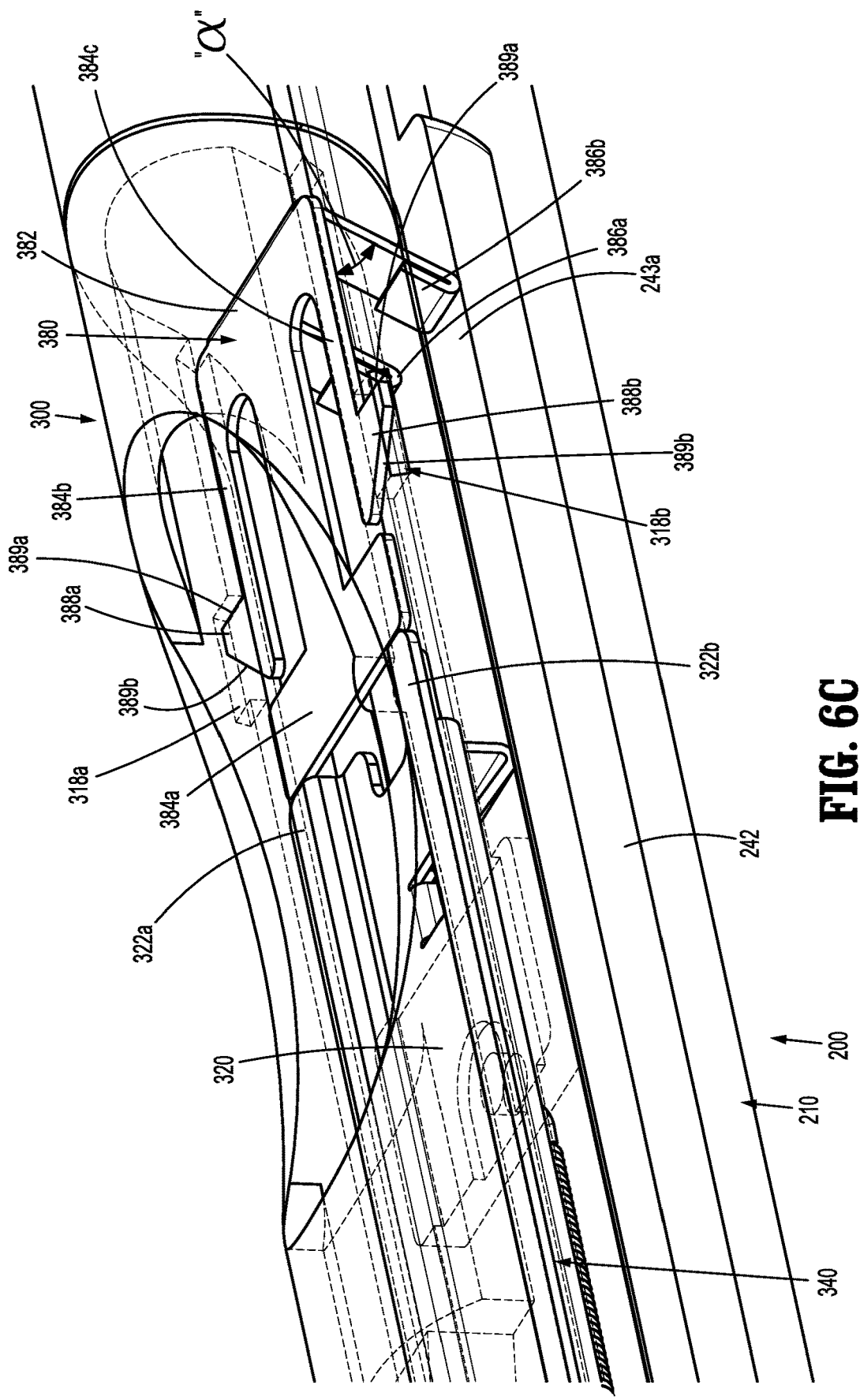

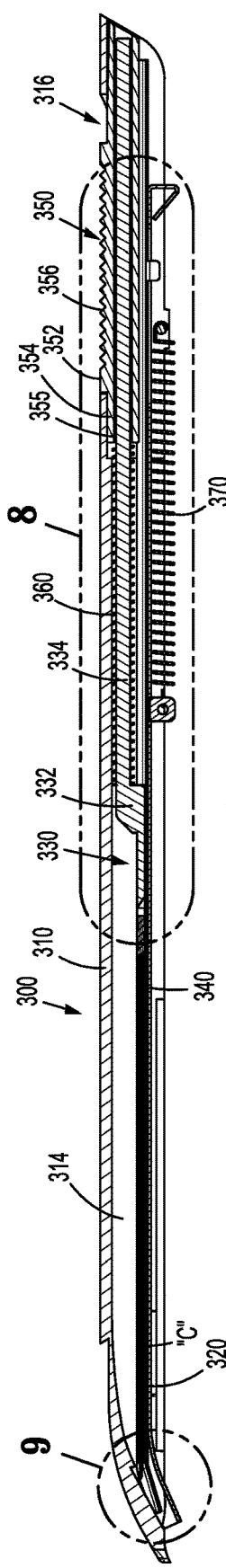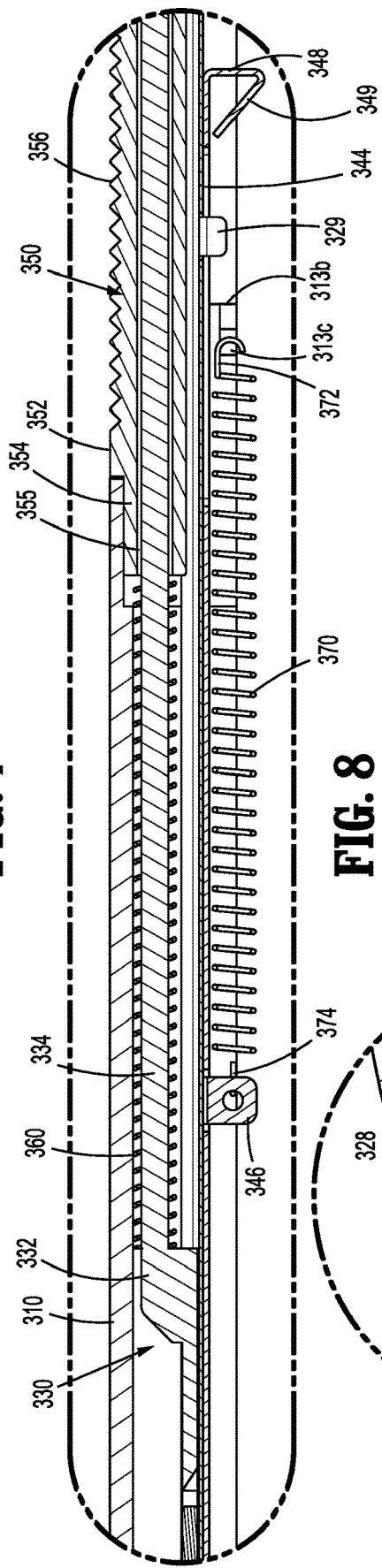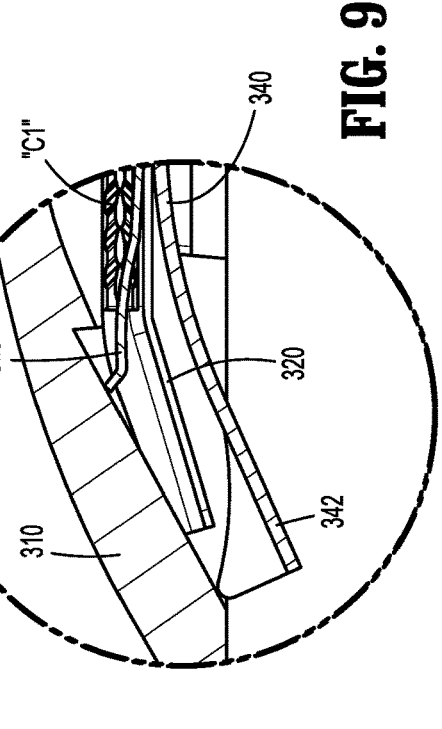

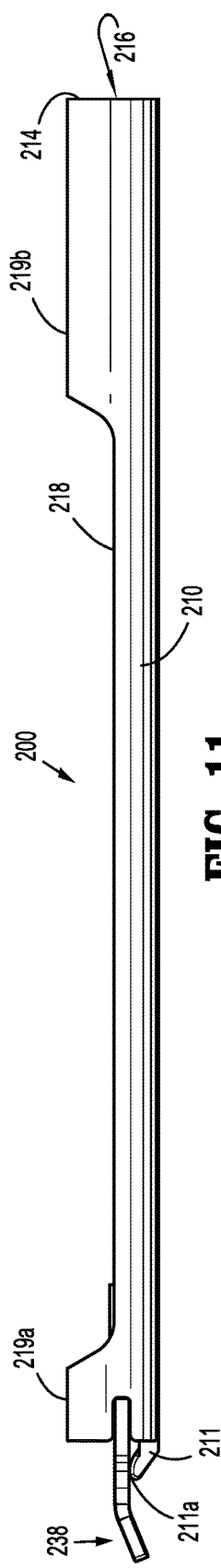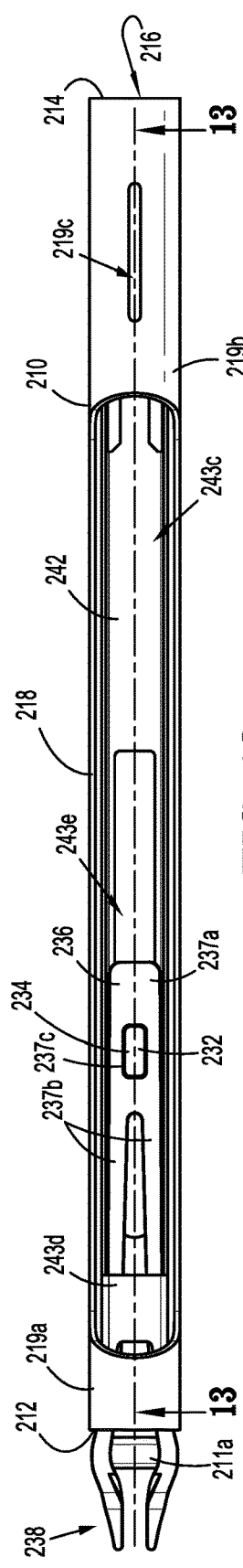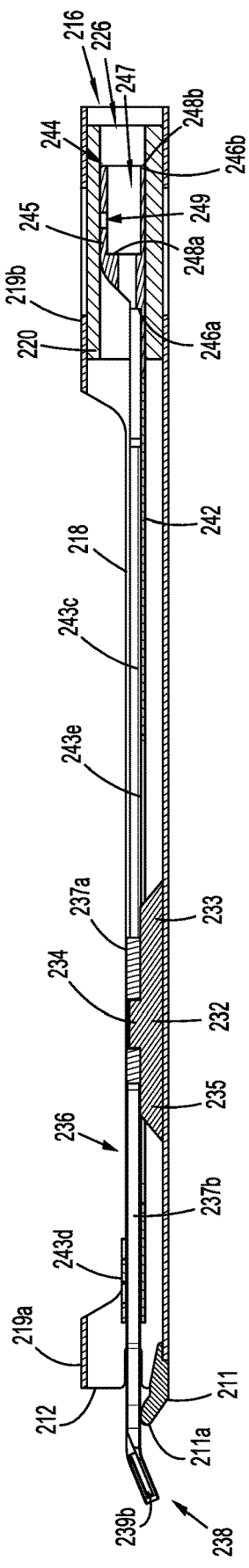

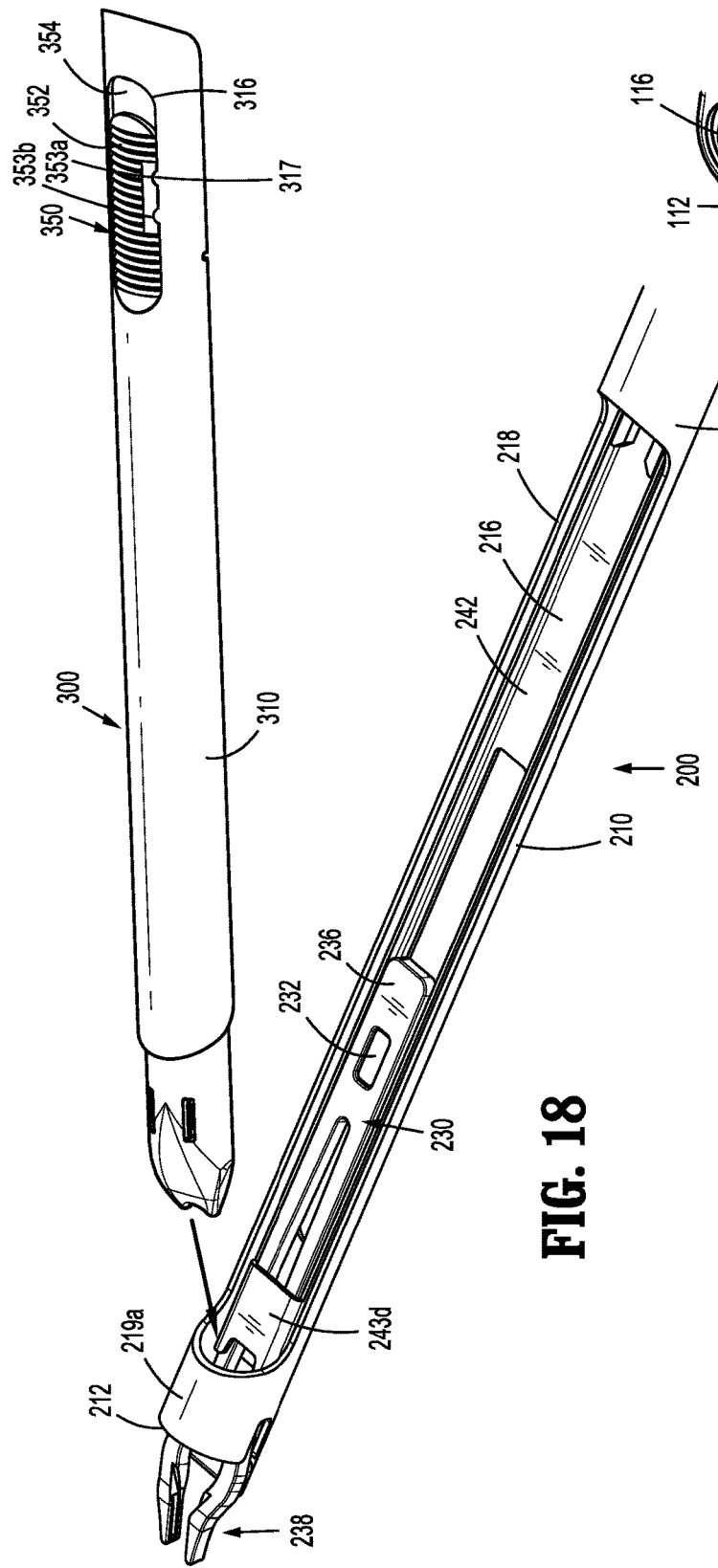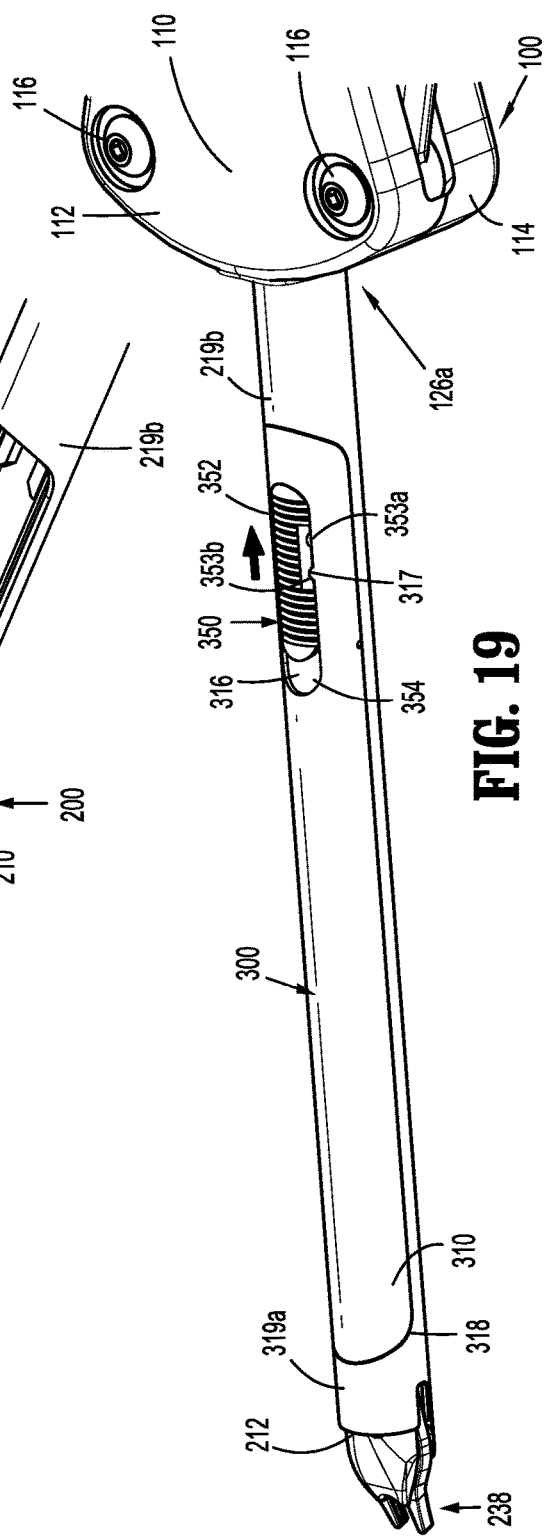
FIG. 18
FIG. 19

REPOSABLE MULTI-FIRE SURGICAL CLIP APPLIER

CROSS-REFERENCE TO RELATED APPLICATION

This application claims the benefit of and priority to U.S. Provisional Patent Application No. 62/598,437 filed Dec. 13, 2017, the entire disclosure of which is incorporated by reference herein.

BACKGROUND

Technical Field

The present disclosure relates to surgical clip appliers and, more particularly, to a reposable multi-fire surgical clip applier including a handle assembly, a shaft assembly, and a clip cartridge assembly that are configured for selective disassembly to facilitate disposal of any disposable component(s) and reprocessing of any reusable component(s) for further use.

Discussion of Related Art

Various staplers and clip appliers are known in the art and used for a number of distinct and useful surgical procedures. Clip appliers that are able to apply multiple clips during a single entry into a body cavity, for example, are described in commonly-assigned U.S. Pat. Nos. 5,084,057 and 5,100,420 to Green et al., the entire contents of which are incorporated herein by reference. Another multiple clip applier is disclosed in commonly-assigned U.S. Pat. No. 5,607,436 by Pratt et al., the entire contents of which is also hereby incorporated herein by reference. U.S. Pat. No. 5,695,502 to Pier et al., the entire contents of which is hereby incorporated herein by reference, discloses a resterilizable surgical clip applier that is configured to receive and cooperate with an interchangeable clip magazine so as to advance and form multiple clips during a single entry into a body cavity.

SUMMARY

The present disclosure relates to a reposable multi-fire surgical clip applier including a handle assembly, a shaft assembly, and a clip cartridge assembly that are configured for selective disassembly to facilitate disposal of any disposable component(s) and reprocessing of any reusable component(s) for further use.

A reposable surgical clip applier provided in accordance with aspects of the present disclosure includes a handle assembly, a shaft assembly releasably engagable with the handle assembly, and a clip cartridge assembly releasably engagable within the shaft assembly.

The handle assembly includes a housing, at least one handle movable relative to the housing between a spaced-apart position and an approximated position, and an inner actuation assembly extending from the housing. The inner actuation assembly includes a proximal drive member movable through the housing, a proximal pusher bar movable through the proximal drive member, and a handle spring assembly. The handle spring assembly includes at least one spring arm engaging the at least one handle to bias the at least one handle towards the spaced apart position. Movement of the at least one handle relative to the housing is configured to move the proximal drive member and the proximal pusher bar in relative opposing directions.

The shaft assembly includes an outer tube, a jaw assembly supported at a distal end portion of the outer tube, and an inner drive slidably disposed within the outer tube and operably coupled to the jaw assembly such that distal movement of the inner drive through the outer tube actuates the jaw assembly.

The clip cartridge assembly retains a stack of surgical clips therein and includes a distal pusher operably coupled to a distal-most surgical clip of the stack of surgical clips such that distal movement of the distal pusher loads the distal-most surgical clip into the jaw assembly when the clip cartridge assembly is releasably engaged within the shaft assembly.

When the shaft assembly is releasably engaged with the handle assembly and the clip cartridge assembly is releasably engaged within the shaft assembly, the proximal drive member is positioned proximally adjacent the inner drive assembly such that movement of the at least one handle towards the approximated position actuates the jaw assembly, and the proximal pusher bar is positioned proximally adjacent the distal pusher such that movement of the at least one handle towards the spaced-apart position loads the distal-most surgical clip into the jaw assembly.

In one aspect of the present disclosure, the handle spring assembly includes a transverse body portion releasably retained within a proximal end portion of the housing. In such aspects, the transverse body portion defines a bore configured to be in communication with the outer tube of the shaft assembly such that, the proximal drive member is movable through the bore of the handle spring assembly to engage the inner drive assembly of the shaft assembly upon movement of the at least one handle.

In embodiments of the present disclosure, the at least one spring arm of the handle spring assembly extends outwardly from the transverse body portion and includes a free proximal end portion. In such embodiments, the free proximal end portion of the at least one spring arm is slidable along the at least handle upon movement of the at least one handle.

In another aspect of the present disclosure, the housing includes at least one internal feature defining a pivot recess configured to movably receive a distal end portion of the at least one handle. In such aspects, the pivot recess and the at least one handle are sized and configured to cooperate to limit movement of the at least one handle beyond a predetermined approximated position and beyond a predetermined spaced-apart position.

In still another aspect of the present disclosure, movement of the at least one handle towards the approximated position moves the proximal drive member distally about the proximal pusher bar and moves the proximal pusher bar proximally about and through the proximal drive member. In such aspects, movement of the at least one handle towards the spaced-apart position moves the proximal drive member proximally about the proximal pusher bar and moves the proximal pusher bar distally about and through the proximal drive member.

In embodiments of the present disclosure, the clip cartridge assembly further includes a biasing member configured to bias the distal pusher proximally.

In aspects of the present disclosure, the clip cartridge assembly further includes a cartridge housing having a support base configured to support at least a portion of the distal pusher. The support base includes a distal bridge portion and a proximal bridge portion. In such aspects, the biasing member of the cartridge assembly is operably coupled to the distal pusher and to the proximal bridge portion to bias the distal pusher proximally.

In another aspect of the present disclosure, the clip cartridge assembly further includes a clip carrier including a pair of engagement flanges. In such aspects, the cartridge housing includes a pair of internal grooves extending longitudinally along at least a portion of a length of the cartridge housing. In such aspects, the pair of internal grooves may be configured to laterally receive the pair of engagement flanges, respectively, to inhibit axial movement of the clip carrier relative to the cartridge housing.

In still another aspect of the present disclosure, the clip cartridge assembly further includes a carrier lock disposed proximally adjacent a proximal end portion of the clip carrier. In such aspects, the carrier lock includes a pair of opposing arms configured to biasingly engage a pair of opposing internal walls of the cartridge housing, wherein the carrier lock is configured to inhibit proximal movement of the clip carrier relative to the cartridge housing beyond the carrier lock.

In embodiments of the present disclosure, the housing of the handle assembly includes an open distal end portion defining a central passageway and a protrusion extending inwardly into the central passageway. In such embodiments, the shaft assembly includes a tubular proximal segment defining a slot configured to receive the protrusion upon insertion of the tubular proximal segment into the open distal end portion to releasably engage the shaft assembly with the handle assembly.

In aspects of the present disclosure, the shaft assembly further includes an inner bushing disposed between the tubular proximal segment and the inner drive assembly. In such aspects, the inner bushing has a slot configured to be axially aligned with the slot of the tubular proximal segment when the inner bushing is disposed therein. In such aspects, the protrusion extending inwardly from the housing is received within the slot of the tubular proximal segment and the slot of the inner bushing.

In another aspect of the present disclosure, the handle assembly includes a pair of handles pivotably coupled to the housing and extending from opposed sides thereof.

In yet another aspect of the present disclosure, the handle spring assembly includes a transverse body portion releasably retained within a proximal end portion of the housing and a pair of spring arms extending outwardly from opposing sides of the transverse body portion. In such aspects, each spring arm of the pair of spring arms are configured to engage a respective handle of the pair of handles to bias the pair of handles towards the spaced-apart position.

In embodiments of the present disclosure, the pair of spring arms each includes a free proximal end portion configured to slide along the respective handle of the pair of handles upon movement of the pair of handles.

In aspects of the present disclosure, the handle assembly further includes a linkage assembly configured to pivotably couple the pair of handles to the inner actuation assembly. In such aspects, the linkage assembly includes a first link arm configured to operably couple a first handle of the pair of handles to the proximal drive member and a second link arm configured to operably couple a second handle of the pair of handles to the proximal pusher bar. In such aspects, upon movement of the pair of handles towards the approximated position, the first link arm is configured to move the proximal drive member distally and the second link arm is configured to move the proximal pusher bar proximally. In such aspects, upon movement of the pair of handles towards the spaced-apart position, the first link arm is configured to move the proximal drive member proximally and the second link arm is configured to move the proximal pusher bar distally.

In another aspect of the present disclosure, the linkage assembly is configured to move the proximal drive member concurrently with the proximal pusher bar upon movement of the pair of handles.

In embodiments of the present disclosure, linkage assembly further includes a third link arm configured to operably couple the second handle of the pair of handles to the proximal drive member and a fourth link arm configured to operably couple the first handle of the pair of handles to the proximal pusher bar.

In another aspect of the present disclosure, the proximal pusher bar is configured to move between the first link arm and the third link arm as the proximal pusher bar moves through the proximal drive member.

A reposable surgical clip applier provided in accordance with another aspect of the present disclosure includes a handle assembly. The handle assembly includes a housing having at least one internal feature, a first and a second handle movable relative to the housing between a spaced-apart position and an approximated position, and an inner actuation assembly disposed within the housing and operably coupled to the first handle and the second handle.

The inner actuation assembly includes a proximal drive member defining a lumen, a proximal pusher bar slidably disposed within the lumen of the proximal drive member and movable in relation to the proximal drive member, a handle spring assembly, and a linkage assembly.

The handle spring assembly includes a transverse body portion supported within the at least one internal feature of the housing and a first spring arm and a second spring arm each extending outwardly from opposing lateral sides of the transverse body portion. The first spring arm is configured to engage the first handle and the second spring arm is configured to engage the second handle, such that, the first handle and the second handle are biased towards the spaced-apart position.

The linkage assembly is configured to pivotably couple the first handle and the second handle to the inner actuation assembly. When the first handle and the second handle are moved relative to the housing, the proximal drive member and the proximal pusher bar are configured to move in relative opposing directions.

In embodiments of the present disclosure, the reposable surgical clip applier further includes a shaft assembly releasably engagable with the handle assembly and a clip cartridge assembly releasably engagable within the shaft assembly.

BRIEF DESCRIPTION OF THE DRAWINGS

Aspects and features of a reposable multi-fire surgical clip applier are provided in accordance with the present disclosure with reference to the drawings wherein:

FIG. 4 is a top view of the clip cartridge assembly of the surgical clip applier of FIG. 3;

FIG. 5 is a bottom view of the clip cartridge assembly of FIG. 4;

FIG. 6A is a cross-sectional view taken across section line "6A-6A" in FIG. 4;

FIG. 6C is a top, perspective view of the area of detail indicated as "6C" in FIG. 1;

FIG. 7 is a longitudinal, cross-sectional view taken across section line "7-7" of FIG. 4;

FIG. 8 is an enlarged, longitudinal, cross-sectional view of the area of detail indicated as "8" in FIG. 7;

FIG. 9 is an enlarged, longitudinal, cross-sectional view of the area of detail indicated as "9" in FIG. 7;

FIG. 11 is a side view of the shaft assembly of FIG. 10;

FIG. 12 is a top view of the shaft assembly of FIG. 10;

FIG. 13 is a longitudinal, cross-sectional view taken across section line "13-13" of FIG. 12;

FIGS. 18 and 19 are top, perspective views illustrating engagement of the clip cartridge assembly of FIG. 3 with the shaft assembly of FIG. 10;

DETAILED DESCRIPTION OF EMBODIMENTS

Figure 1:
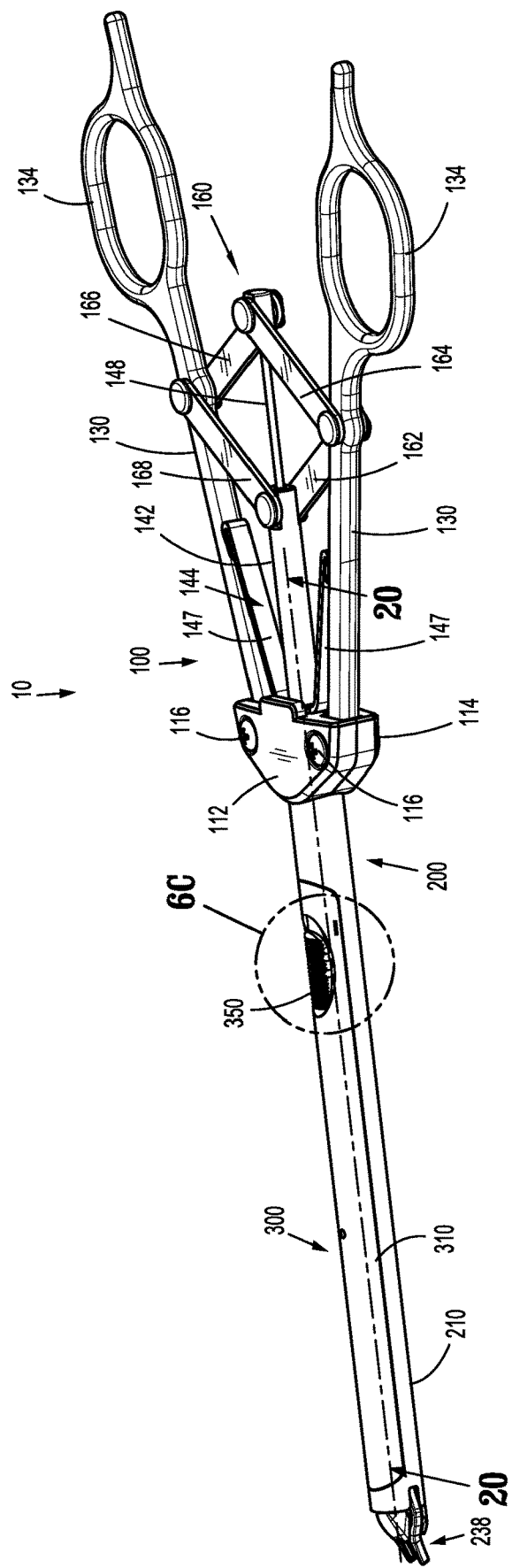
FIG. 1 is a top, perspective view of a reposable multi-fire surgical clip applier provided in accordance with the present disclosure, shown in an assembled condition with a handle assembly thereof in a spaced-apart position.

A reposable multi-fire surgical clip applier in accordance with the present disclosure is described in detail below with reference to the drawing figures wherein like reference numerals identify similar or identical structural elements. As shown in the drawings and described throughout the following description, as is traditional when referring to relative positioning on a surgical instrument, the term "proximal" refers to the end portion of the apparatus or component thereof which is closer to the user and the term "distal" refers to the end portion of the apparatus or component thereof which is further away from the user.

Figure 2:
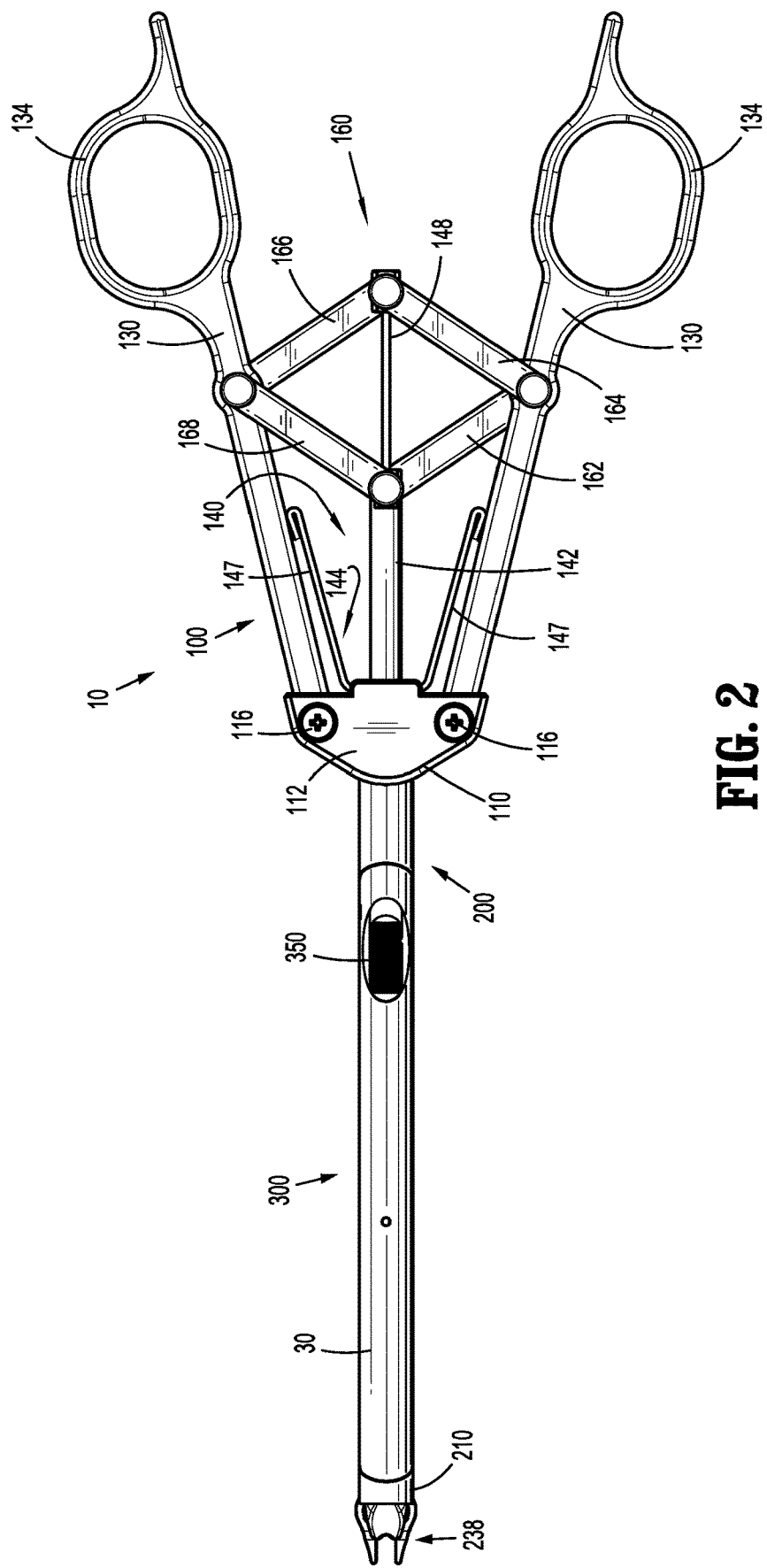
FIG. 2 is a top view of the surgical clip applier of FIG. 1, with the handle assembly thereof in an approximated position.

Referring now to FIGS. 1 and 2, a surgical clip applier in accordance with an embodiment of the present disclosure is generally designated as 10. Surgical clip applier 10 includes a handle assembly 100, a shaft assembly 200 extending distally from handle assembly 100, and a clip cartridge assembly 300 mounted within shaft assembly 200. Shaft assembly 200 is removably and selectively engagable with handle assembly 100 and clip cartridge assembly 300 is removably and selectively mountable within shaft assembly 200. Handle assembly 100 and shaft assembly 200 may be configured as sterilizable, reusable components, while clip cartridge assembly 300 may be configured as a single-procedure-use component. As described in detail below, a stack of surgical clips "C" (FIG. 3) is loaded into clip cartridge assembly 300 such that, in operation, each actuation of handle assembly 100 actuates cooperating drive components of handle assembly 100, shaft assembly 200, and cartridge assembly 300 to fire and form a single surgical clip from the stack of surgical clips "C" (FIG. 3) around a vessel or other tissue to ligate the vessel or other tissue.

Referring to FIGS. 3-9, clip cartridge assembly 300 includes a cartridge housing or housing 310, a clip carrier 320, a clip follower 330, a distal pusher 340, a slider 350, a first biasing member 360, a second biasing member 370, a carrier lock 380, and a stack of surgical clips "C."

Figure 3:
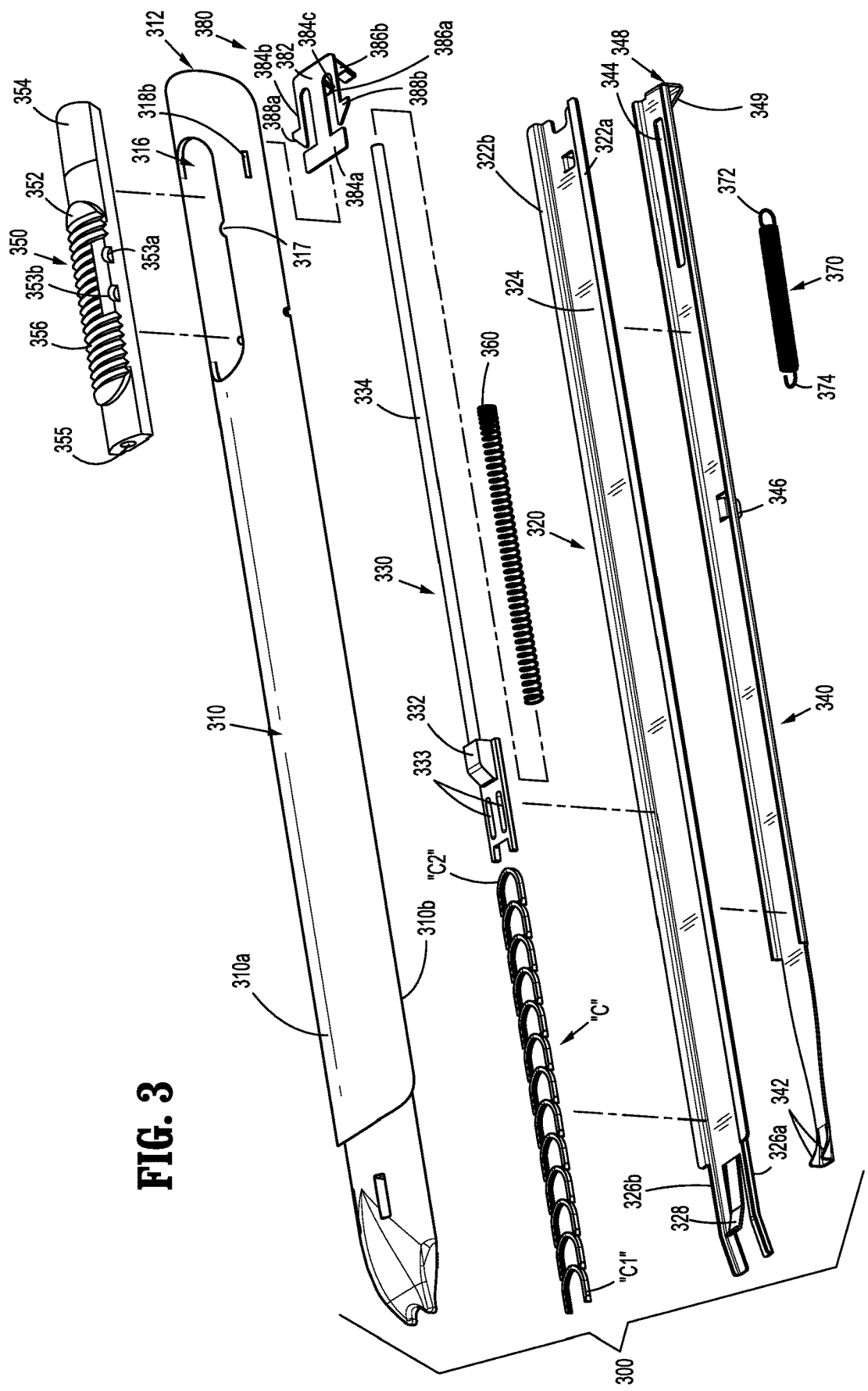
FIG. 3 is a front, perspective view, with parts separated, of a clip cartridge assembly of the surgical clip applier of FIG. 1.
Figure 6B:
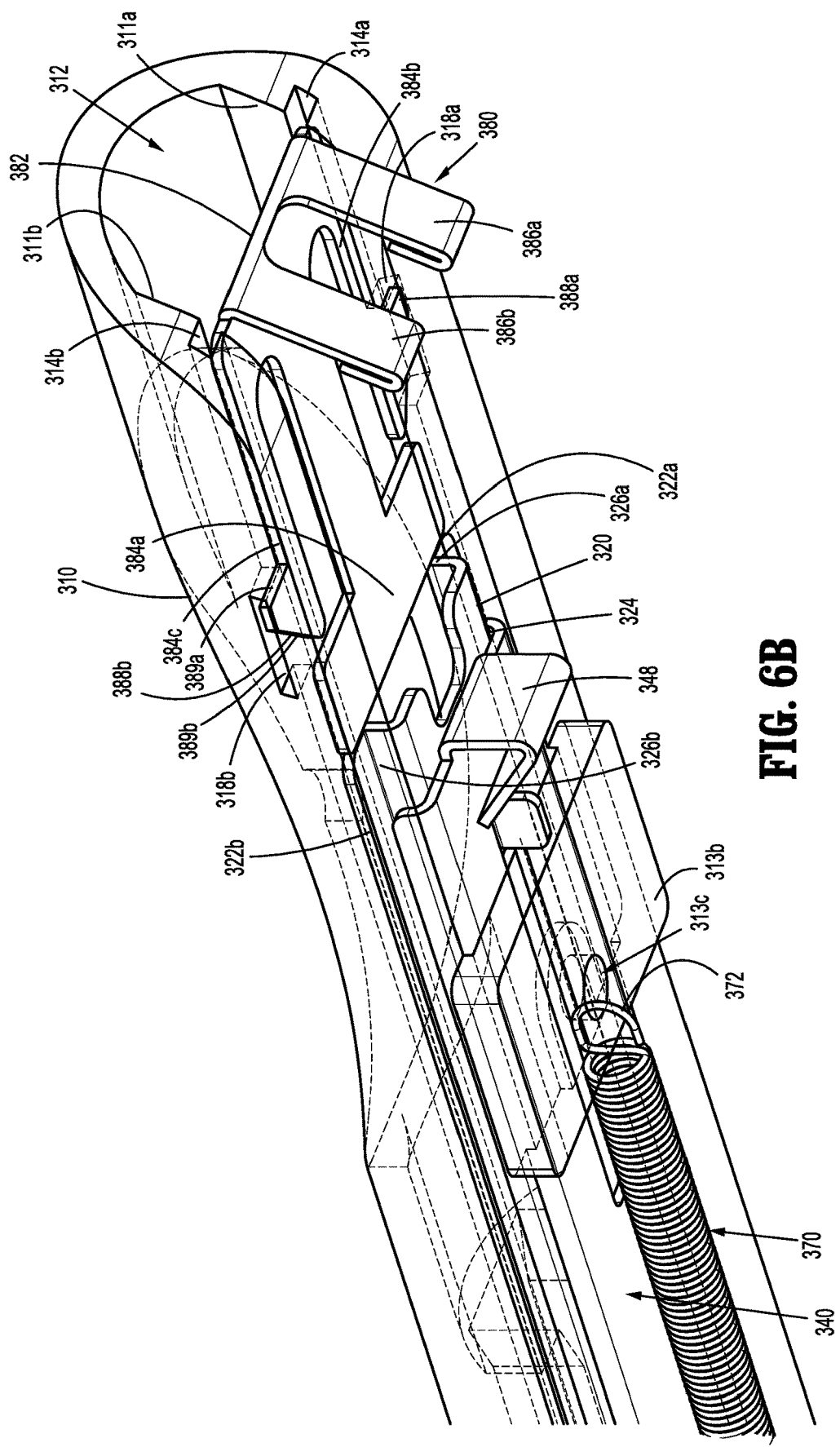
FIG. 6B is a bottom, perspective view of the area of detail indicated as "6B" in FIG. 5.

With reference to FIGS. 3, 6A, and 6B, cartridge housing 310 includes an upper housing portion 310a, a lower housing portion 310b, and an internal cavity 312 extending along a length of the cartridge housing 310 between a distal end portion and a proximal end portion thereof. Cartridge housing 310 may be formed at least partially from a transparent material, such as, for example, a transparent plastic, to enable visualization into internal cavity 312 thereof. Cartridge housing 310 includes a pair of internal grooves 314a, 314b extending longitudinally along at least a portion of the length of the cartridge housing 310, on opposing internal walls 311a, 311b thereof. The pair of internal grooves 314a, 314b are configured to retain clip carrier 320 and carrier lock 380 when clip carrier 320 and carrier lock 380 are disposed within internal cavity 312 of cartridge housing 310, as will be detailed below. Internal cavity 312 of cartridge housing 310 is also configured to receive at least a portion of clip follower 330, distal pusher 340, slider 350, first biasing member 360, second biasing member 370, and the stack of surgical clips "C" therein.

With reference to FIGS. 3-6A, upper housing portion 310a of cartridge housing 310 includes a window 316 formed therein and configured to slidably receive a cap portion 352 of slider 350. Cartridge housing 310 includes a protrusion 317 extending transversely into proximal window 316 from a side thereof. Cap portion 352 of slider 350 defines a more-proximally positioned recess 353a defined on a side thereof and a more-distally positioned recess 353b defined on the same side thereof. More-proximally positioned recess 353a is configured to receive protrusion 317 of cartridge housing 310 to releasably retain slider 350 in a distal position relative to cartridge housing 310. Upon sufficient proximal urging of cap portion 352 of slider 350 relative to cartridge housing 310, protrusion 317 of cartridge housing 310 is dislodged from more-proximally positioned recess 353a of cap portion 352 of slider 350, enabling slider 350 to slide proximally through window 316. Once slider 350 is slid sufficiently proximally, protrusion 317 is engaged within more-distally positioned recess 353b of cap portion 354 of slider 350 to thereby releasably retain slider 350 in a proximal position relative to cartridge housing 310. The proximal and distal positions of slider 350 are described in detail hereinbelow.

With continued reference to FIGS. 3-6A, lower housing portion 310b of cartridge housing 310 includes a support base 313 configured to enclose and support at least a portion of distal pusher 340 when distal pusher is disposed within internal cavity 312 of cartridge housing 310 (FIG. 5). Support base 313 includes a first or distal bridge portion 313a and a second or proximal bridge portion 313b extending between and coupled to lateral sides of cartridge housing 310. In embodiments, the first and second bridge portions 313a, 313b are longitudinally spaced apart and at least a portion of distal pusher 340 is disposed thereon. Second bridge portion 313b includes an aperture or slot 313c configured to receive a proximal end portion 372 of second biasing member 370 thus fixing proximal end portion 372 of second biasing member 370 relative to cartridge housing 310, as will be further detailed below. In embodiments, lower housing portion 310b of cartridge housing 310 may include more than two bridge portions or may be entirely enclosed.

With reference to FIGS. 3, 6A, and 6B, clip carrier 320 of clip cartridge assembly 300 includes a floor 324 and a pair of side walls 326a, 326b extending longitudinally along the opposed sides of floor 324 such that clip carrier 320 defines a generally U-shaped configuration. Clip carrier 320 includes a pair of engagement flanges 322a, 322b configured to engage the pair of internal grooves 314a, 314b of opposing internal walls 311a, 311b, respectively, of cartridge housing 310. Specifically, the pair engagement flanges 322a, 322b extend laterally from the pair of side walls 326a, 326b, respectively, and are disposed within the pair of internal grooves 314a, 314b of cartridge housing 310 to prevent axial movement of clip carrier 320 relative to cartridge housing 310.

As illustrated in FIGS. 6B and 6C, carrier lock 380 includes a body 382 having a central arm 384a, a pair of side arms 384b, 384c disposed on opposing lateral sides of central arm 384a and outwardly biased therefrom, and a pair of legs 386a, 386b folded below and under a proximal end portion of body 382. Each side arm 384b, 384c includes a tang 388a, 388b, respectively, extending outwardly therefrom. Internal cavity 312 of cartridge housing 310 is configured to receive carrier lock 380 such that the pair of side arms 384b, 384c are slidably disposed within internal grooves 314a, 314b, respectively, of cartridge housing 310. Cartridge housing 310 includes a pair of slots 318a, 318b extending through opposing internal walls 311a, 311b. The pair of slots 318a, 318b are positioned and configured to receive the pair of tangs 388a, 388b extending outwardly from the pair of side arms 384b, 384c, respectively, to releasably retain carrier lock 380 within internal cavity 312 of cartridge housing 310.

Each of the pair of tangs 388a, 388b includes a proximal portion 389a that is substantially parallel relative to a respective proximal portion of the pair of slots 318a, 318b and a distal portion 389b that is angled relative to a respective distal portion of the pair of slots 318a, 318b. It is contemplated that during proximal movement of carrier lock 380 relative to cartridge housing 310, the parallel relationship between each of the proximal portions 389a of the pair of tangs 388a, 388b and the respective proximal portions of the pair of slots 318a, 318b will result in an abutting engagement to prevent inadvertent release of the pair of tangs 388a, 388b of carrier lock 380 from within the pair of slots 318a, 318b of internal cavity 312 of cartridge housing 310. Further, it is contemplated that during distal movement of carrier lock 380 relative to cartridge housing 310, the angled relationship between each of the distal portions 389b of the pair of tangs 388a, 388b and the respective distal portions of the pair of slots 318a, 318b will result in a camming engagement to enable release of the pair of tangs 388a, 388b of carrier lock 380 from within the pair of slots 318a, 318b of internal cavity 312 of cartridge housing 310.

With continued reference to FIG. 6B, when clip carrier 320 is disposed within cartridge housing 310, as described above, carrier lock 380 is configured for positioning proximally adjacent a proximal end portion of clip carrier 320 such that central arm 384a of carrier lock 380 is disposed in abutting relation therewith. In this position, since carrier lock 380 is slidably retained within internal cavity 312 via engagement between the pair of tangs 388a, 388b and the pair of slots 318a, 318b, clip carrier 320 is inhibited from moving proximally beyond central arm 384a of carrier lock 380. In this manner, clip carrier 320 is retained within internal cavity 312 of cartridge housing 310.

With additional reference to FIG. 6C, the pair of legs 386a, 386b of carrier lock 380 is folded below and under the proximal end portion of body 382 to define an angle "α" therebetween. In embodiments, angle "α" is less than 90 degrees. This effectively forms a four-bar linkage mechanism providing for easier cleaning and sterilization, all in a more robust design having fewer parts. When cartridge assembly 300 is disposed within shaft assembly 200, as will be detailed below, the pair of legs 386a, 386b of carrier lock 380 is configured to be supported by a base 243a of a distal drive bar 242 of shaft assembly 200.

With additional reference to FIGS. 7-9, clip carrier 320 further includes a resilient central tang 328 extending upwardly from floor 322 towards a distal end portion of clip carrier 320. Resilient central tang 328 is configured to engage a backspan of a distal-most surgical clip "C1" of the stack of surgical clips "C" to retain the stack of surgical clips "C" within clip carrier 320. Clip carrier 320 further includes a leg 329 depending from an underside of floor 322 adjacent a proximal end portion thereof.

With reference to FIGS. 3 and 8, clip follower 330 of clip cartridge assembly 300 includes a distal sled 332 slidably disposed within clip carrier 320 proximally of the stack of surgical clips "C." Distal sled 332 of clip follower 330, more specifically, is configured for positioning proximally adjacent a proximal-most clip "C2" of the stack of surgical clips "C" in abutting relation therewith. Distal sled 332 further defines a pair of slots 333 therethrough, as detailed below. Clip follower 330 further includes an elongated rod 334 extending proximally from distal sled 332. Elongated rod 334 defines a fixed distal end engaged to distal sled 332 and a free proximal end that is slidably disposed within a lumen 355 defined within base portion 354 of slider 350. First biasing member 360 is disposed about elongated rod 334 of clip follower 330 between distal sled 332 and base portion 354 of slider 350 so as to bias distal sled 332 distally into and against the proximal-most clip "C2" of the stack of surgical clips "C," thereby biasing the stack of surgical clips "C" distally. In embodiments, first biasing member 360 may take the form of a coil spring, a constant force spring, a power spring, or another suitable biasing element.

Figure 10:
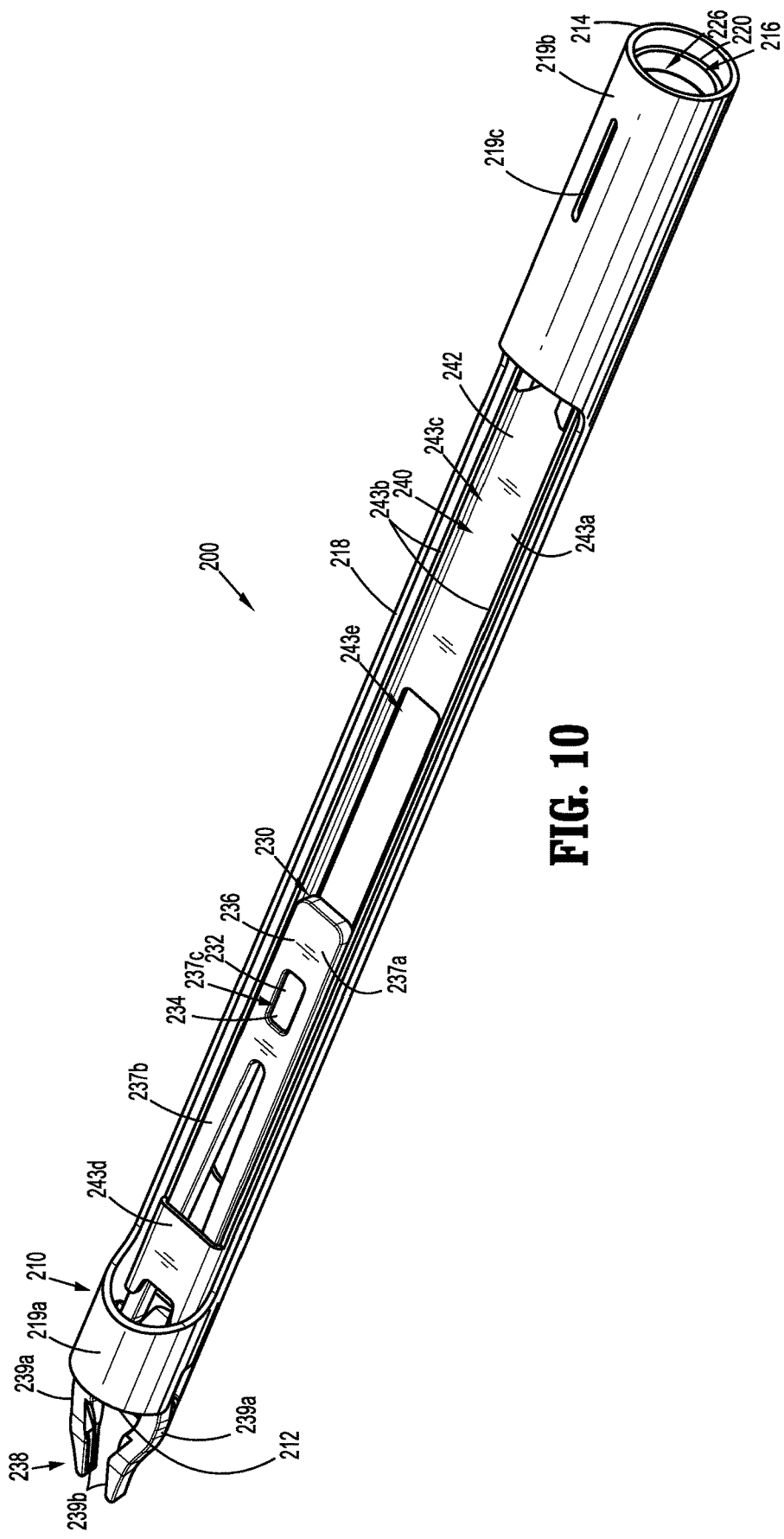
FIG. 10 is a top, perspective view of a shaft assembly of the surgical clip applier of FIG. 1.

With reference to FIGS. 3, 5, and 8, distal pusher 340 of clip cartridge assembly 300 is slidably disposed about an underside of clip carrier 320, opposite clip follower 330. Distal pusher 340 includes a pair of pusher flanges 342 at a distal end portion thereof that are configured to urge the distal-most surgical clip "C1" of the stack of surgical clips "C" distally over resilient central tang 328 of clip carrier 320 and distally from clip cartridge assembly 300 into jaws 238 (FIG. 10). Distal pusher 340 further includes a proximal slot 344 defined therethrough adjacent a proximal end portion thereof that is configured to slidably receive leg 329 of clip carrier 320 to maintain distal pusher 340 and clip carrier 320 in alignment with one another while permitting distal pusher 340 to slide longitudinally relative to clip carrier 320. Specifically, distal pusher 340 is permitted to slide longitudinally relative to clip carrier 320 until a position where leg 329 of clip carrier 320 abuts a proximal end portion or a distal end portion of proximal slot 344 of distal pusher 340.

Distal pusher 340 also includes a flange or tab 346 depending from an underside thereof at an intermediate portion of distal pusher 340. Tab 346 is configured to receive a distal end portion 374 of second biasing member 370 such that the distal end portion 374 of second biasing member 370 is fixed relative to distal pusher 340. With distal end portion 374 of second biasing member 370 fixed relative to distal pusher 340, and with proximal end portion 372 thereof fixed relative to cartridge housing 310 (via slot 313c of second bridge portion 313b, as noted above), second biasing member 370 serves to bias distal pusher 340 proximally relative to cartridge housing 310 and, thus, clip carrier 320 and the stack of surgical clips "C."

Distal pusher 340 additionally includes a proximally-facing pusher surface 348 disposed at the proximal end portion thereof. Proximally-facing pusher surface 348 may be part of a proximal extension 349 that is monolithically formed with distal pusher 340 and folded below and under the proximal end portion thereof to define proximally-facing pusher surface 348.

Referring to FIGS. 3, 7, and 8, slider 350 of clip cartridge assembly 300 includes a base portion 354 and a cap portion 352 disposed on base portion 354. Cap portion 352, as detailed above, is configured for slidable receipt within window 316 of cartridge housing 310 and is releasably engagable therein in either a proximal position or a distal position. In the distal position, base portion 354 of slider 350 does not extend proximally beyond the proximal end portion of cartridge housing 310. In the proximal position, base portion 354 extends proximally beyond the proximal end portion of cartridge housing 310. As detailed below, movement of slider 350 between the distal and proximal position enables selective locking and unlocking of clip cartridge assembly 300 within shaft assembly 200 (FIG. 1).

Base portion 354 of slider 350, as noted above, defines a lumen 355 extending longitudinally therethrough. Lumen 355 is configured to slidably receive elongated rod 334 of clip follower 330, as shown in FIGS. 7 and 8. Cap portion 352 of slider 350 may define a textured, such as, for example, grooved, upper surface 356 to facilitate gripping cap portion 352 of slider 350 to slide slider 350 between the proximal and distal positions.

Continuing with reference to FIG. 3, the stack of surgical clips "C," as detailed above, is supported within clip carrier 320 with the clips thereof arranged in tip-to-tail orientation. Each of the surgical clips of the stack of surgical clips "C" includes a pair of legs interconnected by a backspan. In some embodiments, the stack of surgical clips "C" includes a lockout clip "LC" (FIG. 21) positioned proximally of the proximal-most clip "C2". The lockout clip "LC" is formed as a solid disc and may be distinctively marked and/or colored. Providing the lockout clip "LC" in this manner enables the user to visually determine or at least estimate the number of surgical clips remaining by viewing the position of the lockout clip "LC" through cartridge housing 310. The lockout clip "LC," if loaded into jaws 238 (FIG. 22), also serves as a lockout, as detailed below.

Referring to FIGS. 10-14, shaft assembly 200 includes an outer tube 210, an inner sleeve or bushing 220, a jaw assembly 230, and an inner drive assembly 240. Outer tube 210 includes an open distal end portion 212, an open proximal end portion 214, a lumen 216 extending between and communicating with the open distal and proximal end portions, 212, 214, respectively, and an elongated cut-out 218 defined through a side wall of outer tube 210 and communicating with lumen 216 therethrough. Outer tube 210 further includes a jaws support member 211 extending distally from open distal end portion 212. In embodiments, jaws support member 211 extends distally from a lower portion of outer tube 210 and towards an upper portion of outer tube 210 to define a support surface 211a. Elongated cut-out 218 is spaced-apart from open distal end portion 212 of outer tube 210 such that outer tube 210 defines a tubular distal segment 219a disposed distally of elongated cut-out 218. With brief reference to FIG. 21, in embodiments, tubular distal segment 219a of outer tube 210 may include indicia "I" configured to enable the user to visually determine or at least estimate the number of surgical clips remaining by viewing the position of the lockout clip "LC" through cartridge housing 310. Elongated cut-out 218 is also spaced-apart from open proximal end portion 214 of outer tube 210 such that outer tube defines a tubular proximal segment 219b disposed proximally of elongated cut-out 218. Tubular proximal segment 219b includes an elongated recess or slot 219c configured to engage handle assembly 100 (FIG. 20) to selectively couple shaft assembly 200 and handle assembly 100, as detailed below. In embodiments, tubular proximal segment 219b may include more than one slot 219c.

Figure 14:
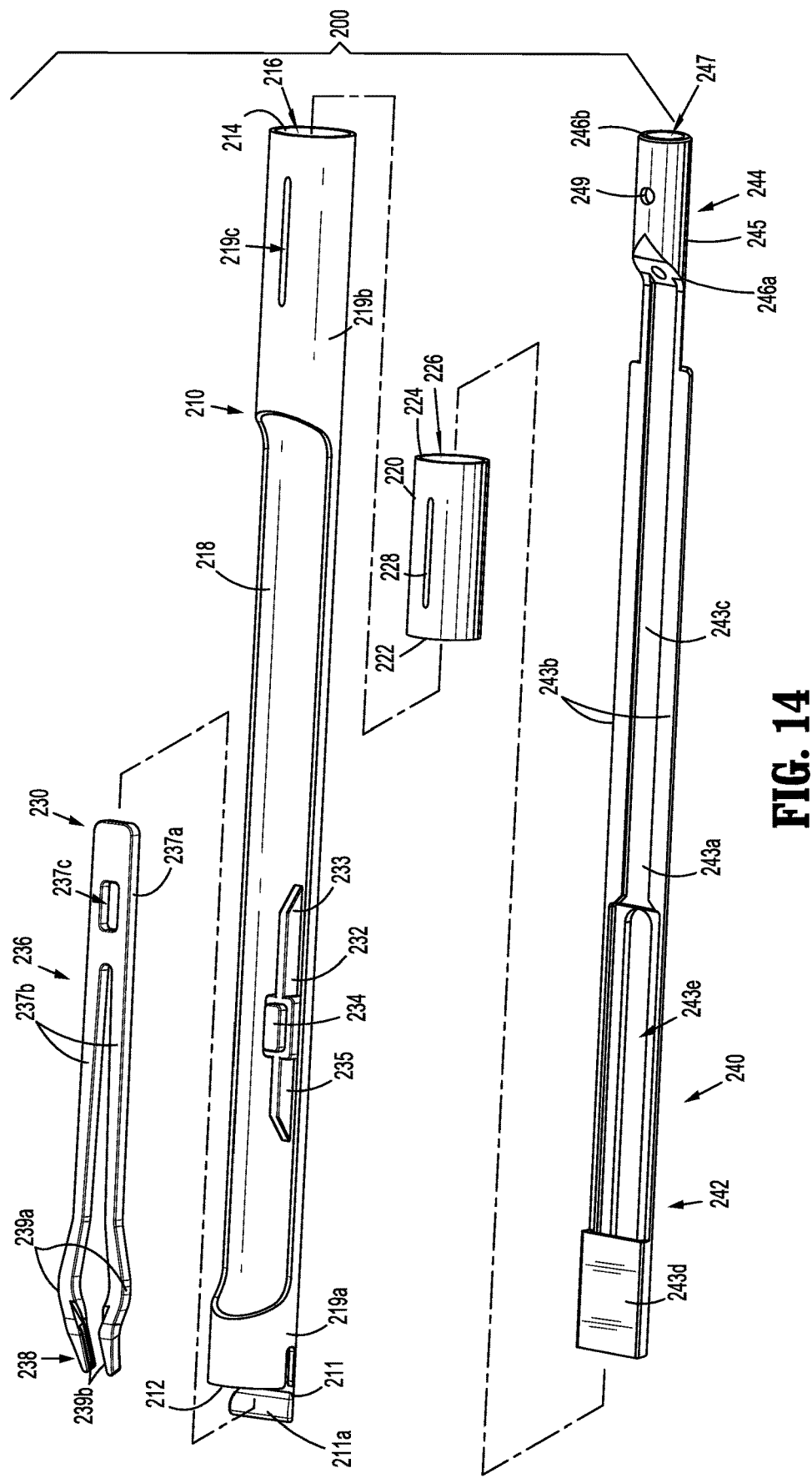
FIG. 14 is a top, perspective view, with parts separated, of the shaft assembly of FIG. 13.

With reference to FIGS. 13 and 14, inner bushing 220 is disposed within tubular proximal segment 219b of outer tube 210. Inner bushing 220 includes an open distal end 222, an open proximal end 224, a lumen 226 extending between and communicating with the open distal and proximal ends, 222, 224, respectively, and an elongated recess or slot 228 defined through a side wall of inner bushing 220. In embodiments, inner bushing 220 may include more than one slot 228. When inner bushing 220 is disposed within tubular proximal segment 219b of outer tube 210, one or more slot(s) 219c of outer tube 210 and one or more slot(s) 228 of inner bushing 220 are sized and aligningly configured to engage handle assembly 100 (FIG. 20) to selectively couple outer tube 210 and inner bushing 220 of shaft assembly 200, with handle assembly 100, as detailed below.

Referring to FIGS. 12 and 14, jaw assembly 230 includes a stationary base 232 and a jaws component 236. Stationary base 232 is affixed within outer tube 210 to an interior surface thereof, via welding or other suitable methods. Stationary base 232 includes a proximal base portion 233, a central block 234, and a distal base portion 235. Jaws component 236 includes a proximal hub 237a, a bifurcated neck 237b, and a pair of jaws 238, one of which is attached to the free distal end of each of the bifurcated portions of bifurcated neck 237b. Proximal hub 237a of jaws component 236 defines a slot 237c configured to receive central block 234 of stationary base 232 to engage and fixedly maintain jaws component 236 within outer tube 210. With jaws component 236 engaged about stationary base 232 in this manner, jaws 238 extend distally from open distal end 212 of outer tube 210.

Jaws 238 of jaw assembly 230 are biased apart from one another via bifurcated neck 237b. Jaws 238 define outwardly-facing cam surfaces 239a and inwardly-facing channels 239b. A distal drive bar 242 of inner drive assembly 240 is configured to engage cam surfaces 239a of jaws 238 and urge jaws 238 towards one another, as detailed below. Inwardly-facing channels 239b of jaws 238 are configured to receive the legs of a surgical clip from the stack of surgical clips "C" therein to retain the surgical clip within the jaws 238 during formation thereof, as also detailed below.

Continuing with reference to FIGS. 10-14, inner drive assembly 240 of shaft assembly 200 includes a distal drive bar 242 and a proximal drive plunger 244. Distal drive bar 242 includes a base 243a and a pair of side walls 243b extending longitudinally along opposing sides of base 243a so as to define an inner channel 243c extending longitudinally along distal drive bar 242.

Distal drive bar 242 of inner drive assembly 240 further includes a boxed distal end portion 243d and a slot 243e defined through base 243a towards the boxed distal end portion 243d thereof. Distal drive bar 242 is slidably disposed within lumen 216 of outer tube 210. Slot 243e of distal drive bar 242 is configured to slidably receive stationary base 232 of jaw assembly 230 therethrough to enable distal drive bar 242 to slide within outer tube 210 and about stationary base 232. Boxed distal end portion 243d of distal drive bar 242 is configured for positioning about bifurcated neck 237b of jaw assembly 230. Upon distal advancement of distal drive bar 242, as detailed below, boxed distal end portion 243d of distal drive bar 242 is advanced distally about jaws component 236 to cam about cam surfaces 239a of jaws 238 to thereby urge jaws 238 towards one another.

Proximal drive plunger 244 of inner drive assembly 240 is slidably disposed within lumen 226 of inner bushing 220, when inner bushing 220 is disposed within tubular proximal segment 219b of outer tube 210. Proximal drive plunger 244 includes a hub 245 having an open distal end portion 246a, an open proximal end portion 246b, and a hub lumen 247 extending between and communicating with the open distal and proximal end portions, 246a, 246b, respectively. Open distal end portion 246a of hub 245 is engaged with a proximal end portion of inner channel 243c of distal drive bar 242 such that hub lumen 247 is in communication with inner channel 243c of distal drive bar 242. Hub 245 includes an inner hub wall 248a adjacent open distal end portion 246a and an outer hub wall 248b adjacent open proximal end portion 246b. Hub lumen 247 extends between and is in communication with inner hub wall 248a and outer hub wall 248b. Hub 245 further includes a threaded opening or bore 249 configured to receive a lock screw 250 (FIG. 20) to releasably fix distal drive bar 242 and an outer drive tube 142 of handle assembly 100, as detailed below.

Jaws component 236 and inner drive assembly 240 are removable from outer tube 210 to facilitate reprocessing of the various components thereof for reuse. In order to insert jaws component 236 and inner drive assembly 240 into operable engagement with outer tube 210 and one another, jaws component 236, led by proximal hub 237a thereof, is inserted proximally through open distal end 212 of outer tube 210 until slot 237c of jaws component 236 is aligned above central block 234 of stationary base 232. Inner bushing 220, led by open distal end portion 246a, is inserted distally through open proximal end 214 of outer tube 210 and slid distally about tubular proximal segment 219b of outer tube 210 until inner bushing 220 is disposed within lumen 216 such that, slot 219c of outer tube 210 and slot 228 of inner bushing 220 are axially aligned. Inner drive assembly 240, led by boxed distal end portion 243d of distal drive bar 242, is inserted distally through open proximal end 214 of outer tube 210 and open proximal end 224 of inner bushing 220, and slid distally about jaws component 236 until boxed distal end portion 243d of distal drive bar 242 is disposed about bifurcated neck 237b of jaws component 236, such that proximal hub 237a of jaws component 236 is disposed above slot 243e of base 243a of distal drive bar 242, and such that hub 245 of proximal drive plunger 244 is disposed within lumen 226 of inner bushing 220.

Once inner drive assembly 240 and jaws component 236 have been positioned as detailed above, proximal hub 237a of jaws component 236 may be engaged with stationary base 232 through slot 243e of base 243a of distal drive bar 242. More specifically, proximal hub 237a of jaws component 236 is urged towards central block 234 of stationary base 232 such that central block 234 is received within slot 237c of jaws component 236. With jaws component 236 engaged with stationary base 232 in this manner, stationary base 232 extends at least partially through slot 243e of base 243a of distal drive bar 242 and boxed distal end portion 243d of distal drive bar 242 is disposed about bifurcated neck 237b of jaws component 236. Thus, outer tube 210, inner bushing 220, jaws component 236, and inner drive assembly 240 are operably engaged with one another. When shaft assembly 200 is assembled as illustrated in FIG. 13, lumen 216 of outer tube 210, lumen 226 of inner bushing 220, and hub lumen 247 of distal drive bar 242 are in communication with one another to slidably receive handle assembly 100, as detailed below. Disengagement and removal of jaws component 236, inner bushing 220, and inner drive assembly 240 from outer tube 210 are effected in the opposite manner of the above-detailed insertion and engagement.

Figure 15:
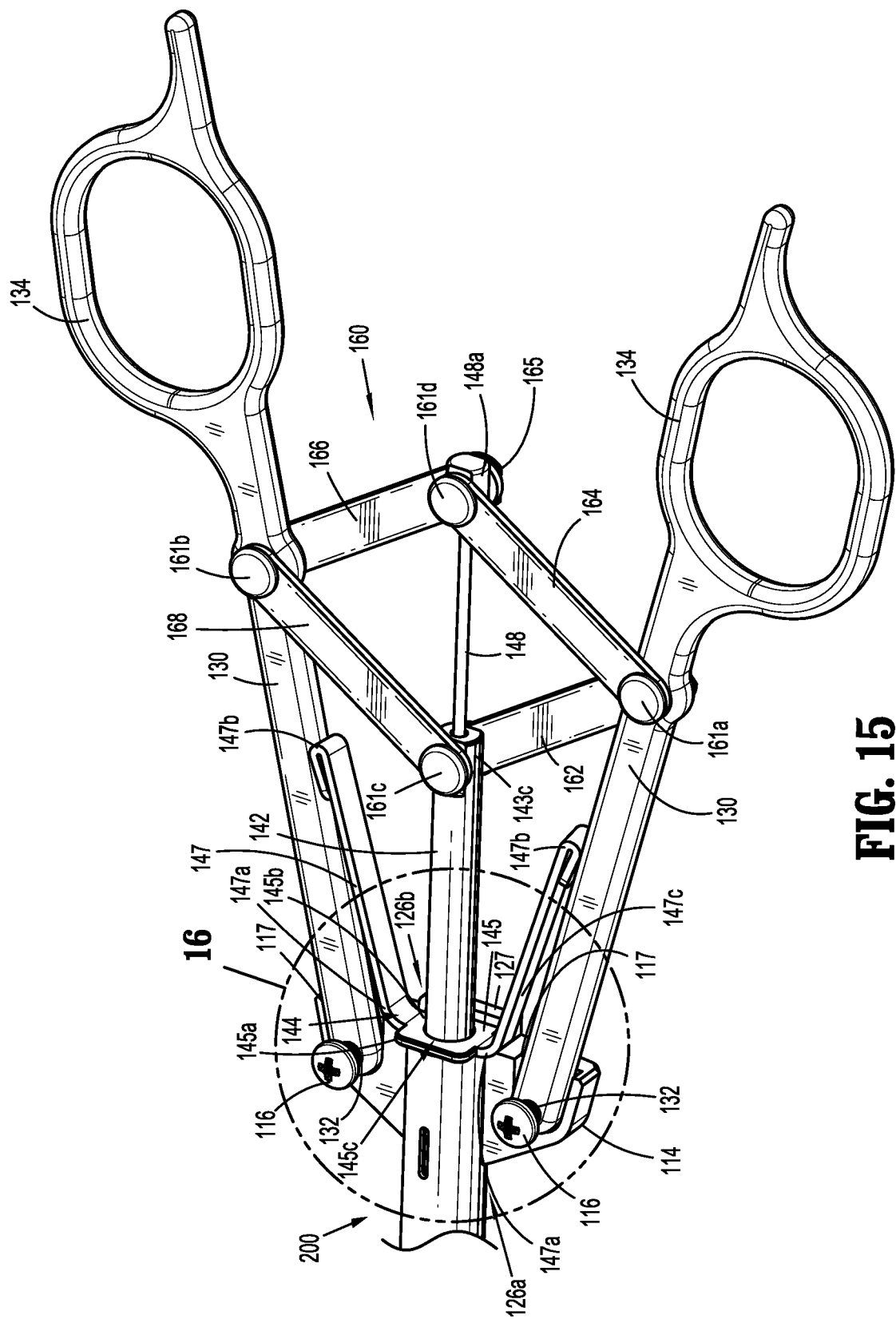
FIG. 15 is a top, perspective view of a handle assembly of FIG. 1, with a housing section removed to illustrate the internal components therein.
Figure 16:
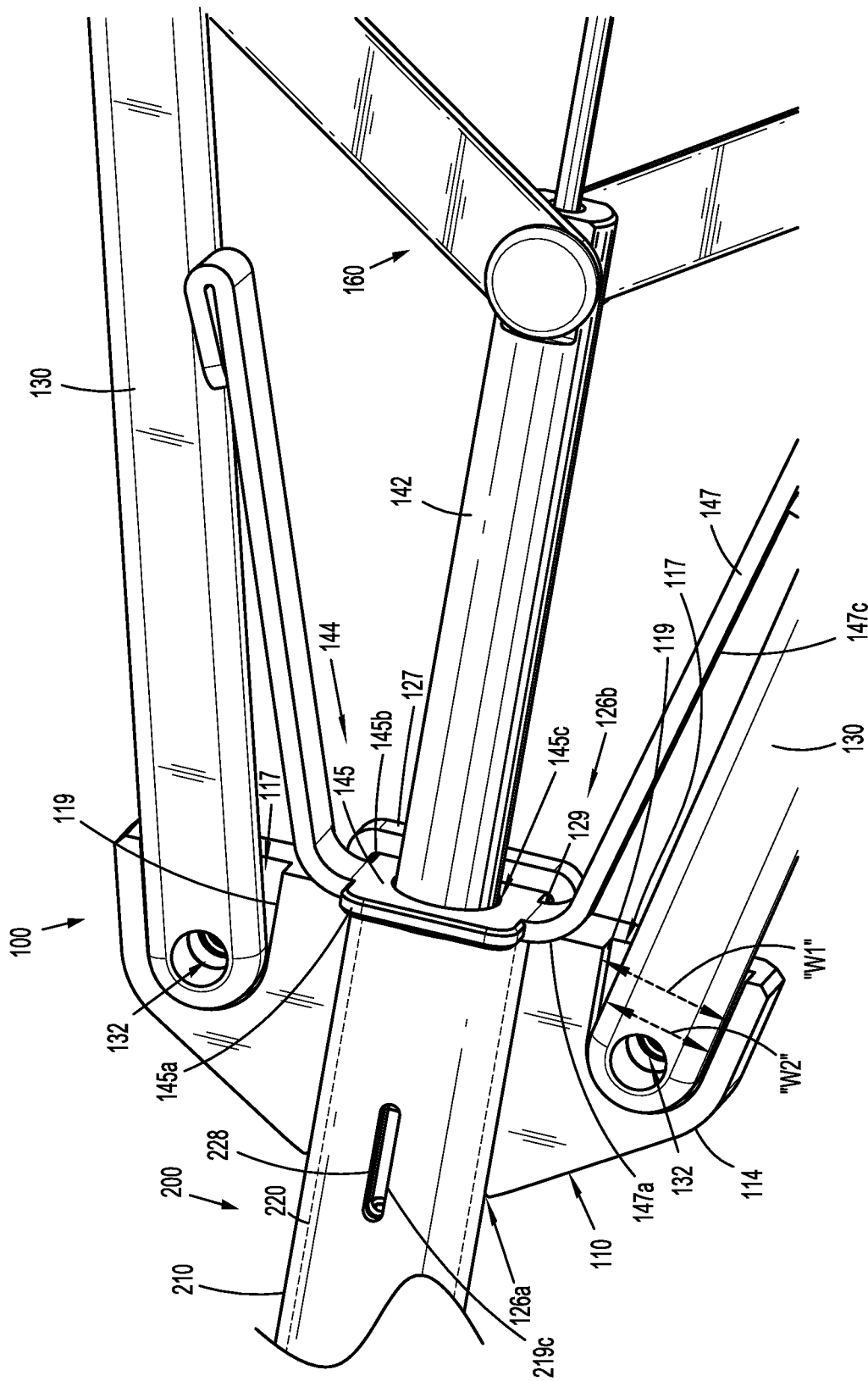
FIG. 16 is an enlarged, top, perspective view of the area of detail indicated as "16" in FIG. 15.

Referring to FIGS. 1, 2, 15-17, and 20, handle assembly 100 includes a housing 110, a pair of handles 130, an inner actuation assembly 140, and a linkage assembly 160. Housing 110 includes an upper housing portion 112 and lower housing portion 114 secured to one another by a plurality of screws 116, although other suitable engagements are also contemplated. As illustrated in FIG. 16, each housing portion 112, 114 further includes a pair of pivot recesses 117 defined by internal features, such as, for example, internal arcuate walls 119. Each pivot recess 117 has a substantially "V" shaped configuration with a tapered distal end portion 117a and an open proximal end portion 117b. Each pivot recess 117 includes a width "W1" adjacent open proximal end portion 117b which gradually decreases towards tapered distal end portion 117a thereof. Pivot recesses 117 are configured to enable movement of the pair of handles 130, respectively, about housing 110 between a spaced-apart position (FIG. 1) and an approximated position (FIG. 2). Respective widths "W1" of each pivot recess 117 and a width "W2" of each handle 130 is configured to cooperate, at least in part, to limit movement of the pair of handles 130 beyond a predetermined maximum spaced-apart position and beyond a predetermined maximum approximated position.

Figure 20:
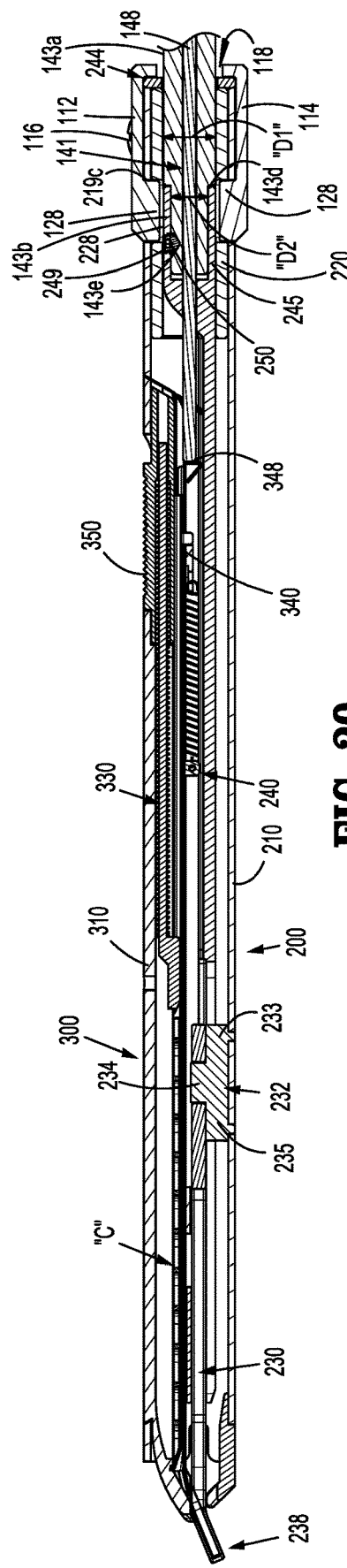
FIG. 20 is a longitudinal, cross-sectional view taken across section line "20-20" of FIG. 1.

With reference to FIGS. 15-17 and 20, housing 110 includes an open distal end portion 126a and an open proximal end portion 126b. Open distal and proximal end portions 126a, 126b are formed from cooperating portions of upper housing portion 112 and lower housing portion 114, and define a central passageway 118 therebetween (FIG. 20). Central passageway 118 is configured to receive a proximal end portion of shaft assembly 200 therethrough to releasably engage shaft assembly 200 with handle assembly 100, as detailed below.

At least one of the upper and lower housing portions 112, 114 includes a tab or protrusion 128 (FIGS. 17 and 20) adjacent open distal end portion 126a and extending radially inwardly into central passageway 118. Protrusion 128 is configured to releasably engage slots 219c, 228 (FIGS. 17 and 20) of tubular proximal segment 219b and inner bushing 220, respectively, such that outer tube 210 and inner bushing 220 are releasably fixed to housing 110, to releasably engage shaft assembly 200 with handle assembly 100, as detailed below.

At least one of the upper and lower housing portions 112, 114 includes a lip 127 extending proximally from open proximal end portion 126b. Lip 127 includes an internal feature, such as, for example, a slot or groove 129. Grooves 129 of each respective lip 127 of upper and lower housing portions 112, 114 cooperate to receive and retain a handle spring assembly 144 of handle assembly 100, as will be detailed below.

Handles 130 of handle assembly 100 are pivotably coupled to housing 110 and extend outwardly from opposing sides thereof. More specifically, each handle 130 includes a pivot bore 132 at the distal end portion thereof and a finger loop 134 at the proximal end portion thereof. Each of the distal end portions of handles 130 are disposed within the respective pivot recess 117 of housing 110 such that the plurality of screws 116 extend through at least one of the upper and lower housing portions 112, 114 and through pivot bores 132 to enable pivoting of handles 130 relative to housing 110 between a spaced-apart position and an approximated position. Finger loops 134 facilitate manipulation of handles 130 to pivot handles 130 between the spaced-apart and approximated positions.

Figure 17:
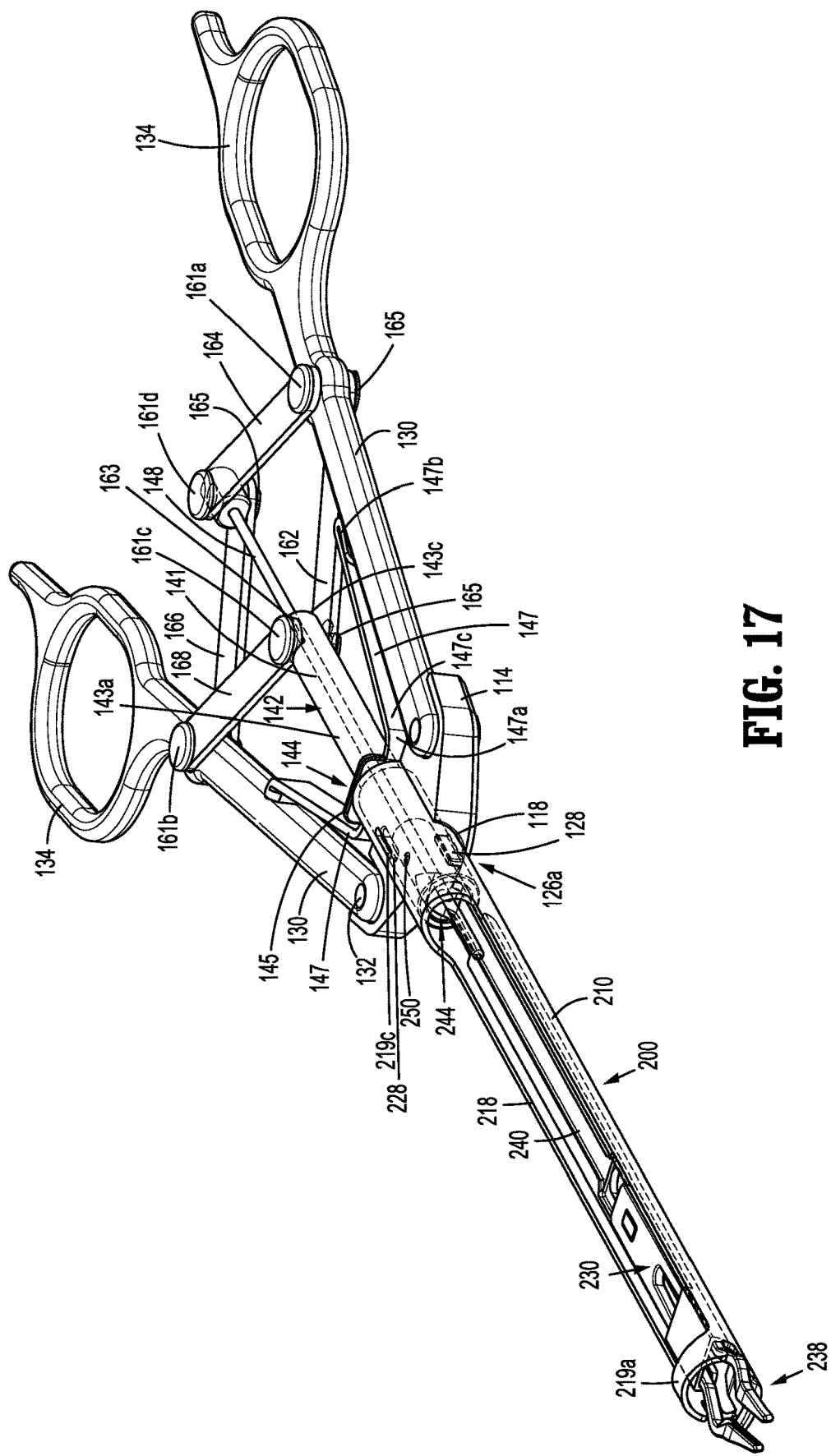
FIG. 17 is a front, perspective view, of the surgical clip applier of FIG. 1, with the clip cartridge assembly removed.

Referring to FIGS. 15, 17, and 20, inner actuation assembly 140 includes a proximal drive member such as, for example, outer drive tube 142, a handle spring assembly 144, and a proximal pusher bar 148. At least a portion of outer drive tube 142 is slidably disposed within housing 110. Outer drive tube 142 includes a body portion 143a, a neck portion 143b extending distally from a distal end portion of body portion 143a, and a substantially flat mounting portion 143c extending proximally from a proximal end portion of body portion 143a. Body portion 143a includes an outer diameter "D1" that is greater than an outer diameter "D2" of neck portion 143b. Body portion 143a includes a shoulder 143d at the distal end portion thereof, defined by the transition from outer diameter "D1" of body portion 143a to outer diameter "D2" of neck portion 143b. Neck portion 143b includes a threaded opening or bore 143e configured to receive lock screw 250 via bore 249 of hub 245 to couple distal drive bar 242 and outer drive tube 142 (FIG. 20). Outer drive tube 142 further includes a lumen 141 (FIG. 20) extending longitudinally therethrough in communication with neck portion 143b and mounting portion 143c. In operation, proximal pusher bar 148 extends through mounting portion 143c of outer drive tube 142, through lumen 141 of outer drive tube 142 in slidable relation relative thereto, and distally from neck portion 143b of outer drive tube 142, as detailed below.

With continued reference to FIGS. 15, 17, and 20, handle spring assembly 144 includes a transverse body portion 145 and a pair of spring arms 147. Transverse body portion 145 includes an upper portion 145a and a lower portion 145b. Upper and lower portions 145a, 145b of transverse body portion 145 are configured to be received within respective grooves 129 of upper and lower housing portions 112, 114 of housing 110 of handle assembly 100 such that transverse body portion 145 of handle spring assembly 144 is fixed between upper and lower housing portions 112, 114 of housing 110. In operation, transverse body portion 145 is disposed proximally adjacent open proximal end portion 214 of outer tube 210 of shaft assembly 200. In embodiments, transverse body portion 145 is disposed proximally abutting open proximal end portion 214 of outer tube 210 of shaft assembly 200. Transverse body portion 145 includes a slot or bore 145c extending therethrough and configured to be in communication with lumen 216 of outer tube 210 of shaft assembly 200. In operation, outer drive tube 142 extends through bore 145c of transverse body portion 145 in slidable relation relative thereto, and engages shaft assembly 200.

Spring arms 147 of handle spring assembly 144 each include a fixed distal end portion 147a coupled to opposing lateral sides of transverse body portion 145 and a free proximal end portion 147b. Spring arms 147 extend outwardly from opposing lateral sides of transverse body portion 145 and are gradually spaced apart. Spring arms 147 are outwardly biased apart and are configured to engage respective handles 130 to urge handles 130 towards the spaced-apart position. Specifically, spring arms 147 each include an inner surface 147c, and at least a portion of the inner surface 147c is configured to maintain contact with, and slide relative to handles 130 when handles 130 are manipulated between the spaced-apart and approximated positions.

Referring to FIG. 15, handle assembly 100 further includes a linkage assembly 160 configured to pivotably couple handles 130 to inner actuation assembly 140. Linkage assembly 160 includes a first link arm 162, a second link arm 164, a third link arm 166, and a fourth link arm 168. Each of the first and second link arms 162, 164 are pivotably coupled at a first end portion thereof to an intermediate portion of one of the handles 130 via a first pivot boss 161a and each of the third and fourth link arms 166, 168 are pivotably coupled at a first end portion thereof to an intermediate portion of the other of the handles 130 via a second pivot boss 161b. Each of the first and fourth link arms 162, 168 are internally pivotably coupled at mounting portion 143c of outer drive tube 142 adjacent the proximal end portion of body 143a via a third pivot boss 161c. Each of the second and third link arms 164, 166 are internally pivotably coupled at a second end portion thereof to a pusher mount 148a adjacent the proximal end portion of proximal pusher bar 148 via a fourth pivot boss 161d. As illustrated in FIG. 17, third pivot boss 161c includes a bore 163 extending therethrough and configured to be in communication with lumen 141 of outer drive tube 142. In operation, proximal pusher bar 148 extends through bore 163 of third pivot boss 161c, in slidable relation thereto, and distally through lumen 141 of outer drive tube 142.

In embodiments, first, second, third, and fourth link arms 162, 164, 166, and 168 are disposed such that each of the intermediate portions of handles 130, mounting portion 143c of outer drive tube 142, and pusher mount 148a of proximal pusher bar 148 are sandwiched between respective portions of first, second, third, and fourth link arms 162, 164, 166, and 168 as described above. In embodiments, each of the first, second, third, and fourth pivot bosses 161a, 161b, 161c, and 161d includes a locking element 165 configured to inhibit axial movement and inadvertent release of the first, second, third, and fourth pivot bosses 161a, 161b, 161c, and 161d when linkage assembly 160 is assembled as described above.

Referring to FIGS. 15 and 17, in operation, with handles 130 disposed in the spaced-apart position relative to housing 110, outer drive tube 142 is disposed in a proximal-most position, while proximal pusher bar 148 is disposed in a distal-most position. As handles 130 are pivoted towards housing 110, towards the approximated position, first and fourth link arms 162, 168 urge outer drive tube 142 distally, and second and third link arms 164, 166 pull proximal pusher bar 148 proximally. It is contemplated that as handles 130 are pivoted towards the approximated position, linkage assembly 160 is configured to move outer drive tube 142 concurrently with proximal pusher bar 148. With handles 130 disposed in the approximated position relative to housing 110, outer drive tube 142 is disposed in a distal-most position, while proximal pusher bar 148 is disposed in a proximal-most position.

During the above-noted pivoting of handles 130 towards the approximated position, spring arms 147 of handle spring assembly 144 engage the handles 130 such that handles 130 are moved through an actuation stroke against the outward bias of spring arms 147. As noted earlier, the predetermined maximum approximated position is determined, at least in part, by the cooperation between width "W1" of each pivot recess 117 of housing 110 and width "W2" of each handle 130, respectively (FIG. 16).

Upon release or return of handles 130 towards the spaced-apart position relative to housing 110, handles 130 move first and fourth link arms 162, 168 to pull outer drive tube 142 proximally, and move second and third link arms 164, 166 to urge proximal pusher bar 148 distally. It is contemplated that as handles 130 are pivoted towards the spaced-apart position, linkage assembly 160 is configured to move outer drive tube 142 concurrently with proximal pusher bar 148. With handles 130 disposed in the spaced-apart position relative to housing 110, outer drive tube 142 is disposed in the proximal-most position, while proximal pusher bar 148 is disposed in the distal-most position.

During the above-noted return of handles 130 towards the spaced-apart position, spring arms 147 of handle spring assembly 144 engage the handles 130 such that handles 130 are moved through a return stroke with the outward bias of spring arms 147. Accordingly, the bias of handle spring assembly 144 is configured to pull outer drive tube 142 proximally and urge proximal pusher bar 148 distally. As noted earlier, the predetermined maximum spaced-apart position is determined, at least in part, by the cooperation between width "W1" of each pivot recess 117 of housing 110 and width "W2" of each handle 130, respectively (FIG. 16).

Turning now to FIGS. 1 and 17-20, in order to assemble surgical clip applier 10 for use, handle assembly 100, shaft assembly 200, and clip cartridge assembly 300, if not preassembled, are individually assembled, as detailed above. Thereafter, shaft assembly 200 is engaged with handle assembly 100, as detailed below.

With reference to FIGS. 17 and 20, in order to engage shaft assembly 200 with handle assembly 100, the proximal end portion of shaft assembly 200 is inserted proximally into open distal end portion 126a of housing 110. More specifically, shaft assembly 200 is moved proximally relative to handle assembly 100 such that tubular proximal segment 219b of shaft assembly 200 is inserted proximally into central passageway 118 until protrusion 128 is received within slots 219c, 228 of tubular proximal segment 219b and inner bushing 220, respectively, to thereby releasably engage shaft assembly 200 with handle assembly 100. In embodiments, if housing 110 is preassembled, the plurality of screws 116 may be removed or loosened to space apart upper housing portion 112 and lower housing portion 114 such that slots 219c, 228 of tubular proximal segment 219b and inner bushing 220, respectively, may be aligned with protrusion 128. Once protrusion 128 is received within slots 219c, 228 of tubular proximal segment 219b and inner bushing 220, respectively, upper housing portion 112 and lower housing portion 114 may be secured to one another by the plurality of screws 116.

During the above-noted insertion of the proximal end portion of shaft assembly 200 into open distal end portion 126a of housing 110, outer drive tube 142 and proximal pusher bar 148 disposed within lumen 141 of outer drive tube 142, are received within and extends through hub lumen 247 of hub 245 of proximal drive plunger 244 of inner drive shaft 240 of shaft assembly 200. When shaft assembly 200 engages with handle assembly 100 as detailed above, neck portion 143b of outer drive tube 142 is positioned proximally adjacent inner hub wall 248a of hub 245 of proximal drive plunger 244 and shoulder 143d of outer drive tube 142 is positioned proximally adjacent outer hub wall 248b of hub 245 of proximal drive plunger 244. With neck portion 143b of outer drive tube 142 disposed within hub 245 of distal drive bar 242, lock screw 250 is disposed within bore 249 of hub 245 and bore 143e of neck portion 143b to releasably fix distal drive bar 242 and outer drive tube 142.

Further, when shaft assembly 200 engages with handle assembly 100 as detailed above, proximal pusher bar 148 extends through lumen 141 of body 143a and neck portion 143b of outer drive tube 142 in slidable relation relative thereto, distally from open distal end portion 246a of hub 245. Once shaft assembly 200 is engaged with handle assembly 100, clip cartridge assembly 300 may be engaged within shaft assembly 200, as detailed below.

Referring to FIGS. 18 and 19, to engage clip cartridge assembly 300 within shaft assembly 200, slider 350 of clip cartridge assembly 300, if not already in the distal position, is moved to the distal position, wherein base portion 354 of slider 350 does not extend proximally beyond the proximal end portion of cartridge housing 310 and wherein more-proximally positioned recess 353a of cap portion 352 of slider 350 is engaged within protrusion 317 of cartridge housing 310 to retain slider 350 in the distal position.

With reference to FIG. 18, with slider 350 in the distal position, clip cartridge assembly 300 is inserted through elongated cut-out 218 of outer tube 210 of shaft assembly 200 and distally relative to outer tube 210 such that the distal end portion of cartridge housing 310 ducks under tubular distal segment 219a of outer tube 210 and extends through the portion of lumen 216 defined by tubular distal segment 219a of outer tube 210. Following the positioning of the distal end portion of cartridge housing 310 in this manner, the remainder of clip cartridge assembly 300 is inserted through elongated cut-out 218 to be seated within lumen 216 of outer tube 210.

Referring to FIGS. 7, 8, and 19, once clip cartridge assembly 300 is fully seated within lumen 216 of outer tube 210 with the distal end portion of cartridge housing 310 extending through tubular distal segment 219a of outer tube 210, slider 350 is urged proximally such that protrusion 317 of cartridge housing 310 is dislodged from more-proximally positioned recess 353a of cap portion 352 of slider 350, slider 350 is slid proximally through window 316, and protrusion 317 is engaged within more-distally positioned recess 353b of cap portion 352 of slider 350 to retain slider 350 in the proximal position.

In the proximal position of slider 350, base portion 354 of slider 350 extends proximally beyond the proximal end portion of cartridge housing 310 and into tubular proximal segment 219b of outer tube 210. Thus, with base portion 354 of slider 350 extending into tubular proximal segment 219b of outer tube 210 and the distal end portion of cartridge housing 310 extending through tubular distal segment 219a of outer tube 210, clip cartridge assembly 300 is locked in engagement within shaft assembly 200. Disengagement and removal of clip cartridge assembly 300 is effected in the opposite manner as the insertion and engagement detailed above.

With additional reference to FIG. 2, handles 130 of handle assembly 100 are moved to and maintained in the approximated position during the above-noted insertion of clip cartridge assembly 300 into shaft assembly 200, although handles 130 need not be maintained in the approximated position during movement of slider 350 to lock clip cartridge assembly 300 within shaft assembly 200.

By maintaining handles 130 of handle assembly 100 in the approximated position during insertion of clip cartridge assembly 300 into shaft assembly 200, proximal pusher bar 148 is disposed in a proximal-most position such that, proximal pusher bar 148 does not interfere with the insertion of clip cartridge assembly 300 into shaft assembly 200. Rather, proximal pusher bar 148, in the proximal-most position thereof, is maintained proximally of proximally-facing pusher surface 348 of distal pusher 340 of clip cartridge assembly 300.

Referring to FIGS. 1, 3, 7-9, 13, and 20, once clip cartridge assembly 300 is disposed within shaft assembly 200, handles 130 may be released or returned towards the spaced-apart position (FIG. 1) such that proximal pusher bar 148 is moved distally through lumen 141 of outer drive tube 142 and towards the distal-most position of proximal pusher bar 148. As proximal pusher bar 148 is moved distally, a distal end portion of proximal pusher bar 148 is urged into proximally-facing pusher surface 348 of distal pusher 340 to thereby urge distal pusher 340 distally. As distal pusher 340 is moved distally, pusher flanges 342 thereof engage a backspan of a distal-most surgical clip "C1" of the stack of surgical clips "C" and urge the distal-most surgical clip "C1" distally over resilient central tang 328 of clip carrier 320 and distally from clip cartridge assembly 300 into inwardly-facing channels 239b of jaws 238. Thus, surgical clip applier 10 is loaded with a surgical clip within jaws 238 and ready for use (FIG. 9). As the distal-most clip of the stack of surgical clips "C" is loaded into jaws 238, sled 332 of clip follower 330, under the bias of first biasing member 360, urges the remaining clips, in the stack of surgical clips "C", distally such that each clip takes the position previously occupied by its distally-adjacent clip.

In use, with general reference to FIGS. 1, 2, 13, and 20-22, surgical clip applier 10 is manipulated such that a vessel (or other tissue), to be ligated, is disposed between jaws 238. Once this position has been achieved, handles 130 are moved from the spaced-apart position (FIG. 1) towards the approximated position (FIG. 2). As detailed above, as handles 130 are moved towards the approximated position against the bias of handle spring assembly 144, outer drive tube 142 is urged distally. As outer drive tube 142 is urged distally, proximal drive plunger 244, which is coupled to outer drive tube 142 via lock screw 250, is in turn moved distally to thereby urge distal drive bar 242 distally. As distal drive bar 242 is advanced distally, boxed distal end portion 243d of distal drive bar 242 is advanced distally to cam about cam surfaces 239a of jaws 238, thereby urging jaws 238 towards one another to form the surgical clip loaded therein about the vessel (or other tissue).

Once the surgical clip is formed about the vessel (or other tissue), handles 130 may be released or returned towards the spaced-apart position such that the next distal-most surgical clip "C1" of the stack of surgical clips "C" is loaded into jaws 238 for subsequent firing. The above-detailed use of surgical clip applier 10 may be repeated to fire a plurality of surgical clips from the stack of surgical clips "C" until only the lockout clip "LC" remains.

Figure 21:
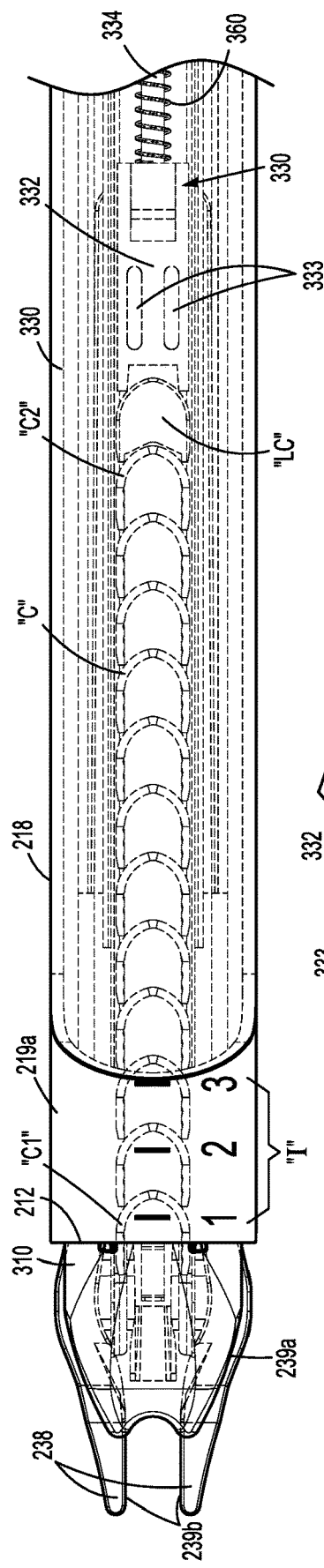
FIG. 21 is a top view of a distal portion of the surgical clip applier of FIG. 1.
Figure 22:
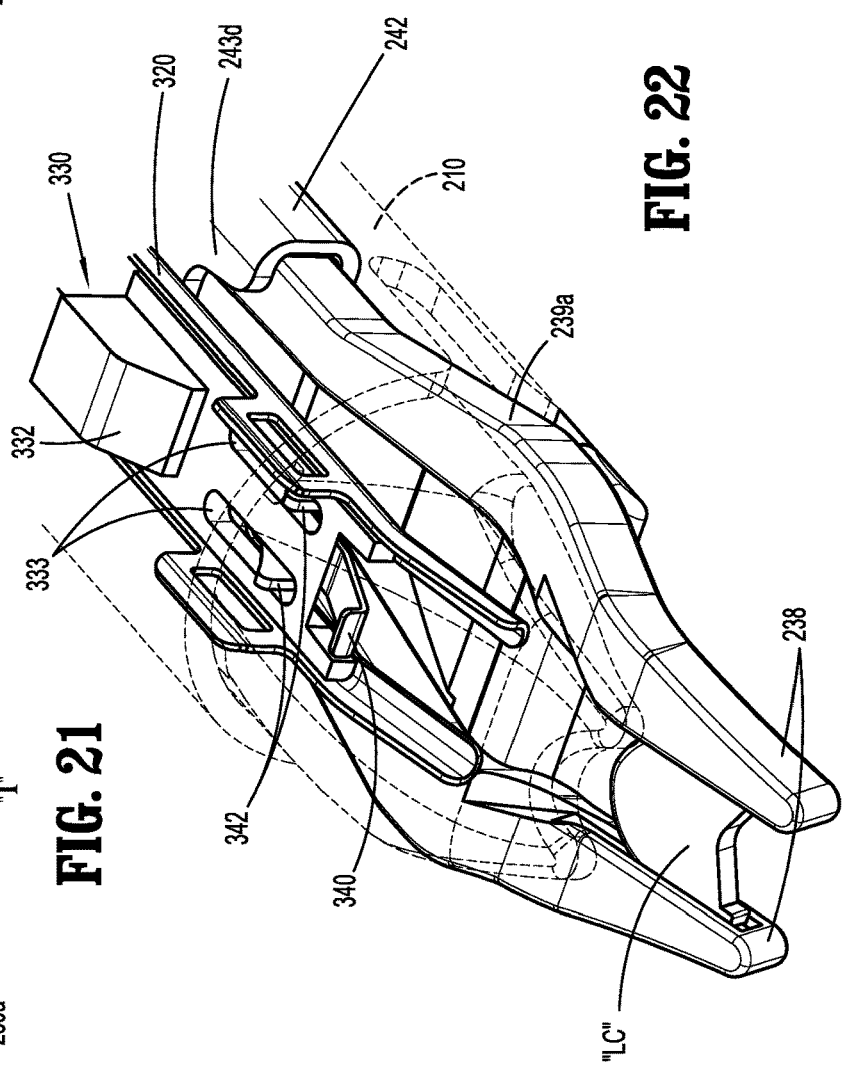
FIG. 22 is an enlarged, front, perspective view of a distal end portion of the surgical clip applier of FIG. 1 with components shown in phantom to illustrate internal features of the surgical clip applier.

Referring to FIGS. 1, 21, and 22, once the proximal-most clip "C2", the surgical clip disposed distally adjacent the lockout clip "LC," has been fired and handles 130 are released or returned towards the spaced-apart position, distal pusher 340 is moved distally such that pusher flanges 342 thereof engage a proximally-facing edge of the lockout clip "LC" and urges the lockout clip "LC" distally from clip cartridge assembly 300 into inwardly-facing channels 239b of jaws 238. Since the lockout clip "LC" is formed as a solid disc, jaws 238 are inhibited from being moved towards one another when the lockout clip "LC" is disposed therebetween. Thus, actuation of handles 130 is inhibited. Further, with no clips remaining in clip cartridge assembly 300, sled 332 of clip follower 330 is moved to the distal end portion of clip carrier 320 under the bias of first biasing member 360. As a result of this configuration, as pusher flanges 342 are moved proximally in response to the release or return of handles 130 towards the spaced-apart position, pusher flanges 342 are engaged within slots 333 of sled 332 of clip follower 330 to further inhibit subsequent actuation of handles 130. Thus, clip-less firing of surgical clip applier 10 is inhibited.

The present disclosure contemplates that surgical clip applier 10 be capable of loading different surgical clip cartridge assemblies 300 within shaft assembly 200. Specifically, surgical clip applier 10 may be loaded with a clip cartridge assembly 300 having a stack of surgical clips "C" of a particular size and/or configuration. For example, depending upon a particular purpose, a first clip cartridge assembly 300 having a stack of surgical clips "C" of a first size or a second clip cartridge assembly 300 having a stack of surgical clips "C" of a second size different than the first size may be loaded into shaft assembly 200. Additionally, during a surgical procedure, if the need arises to use a different size and/or configuration of surgical clip, the user may remove the clip cartridge assembly 300 being used in favor of a different clip cartridge assembly 300.

The present disclosure further contemplates a surgical kit including one handle assembly 100, one shaft assembly 200, and one or more clip cartridge assemblies 300 (similar or different from one another). The kit may also include instructions for the assembly of surgical clip applier 10, the use of surgical clip applier 10, and/or the reprocessing of reusable components of surgical clip applier 10 following use. A package, container, or box may also be provided.

Surgical instruments such as the clip applier(s), or components thereof, described herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 23:
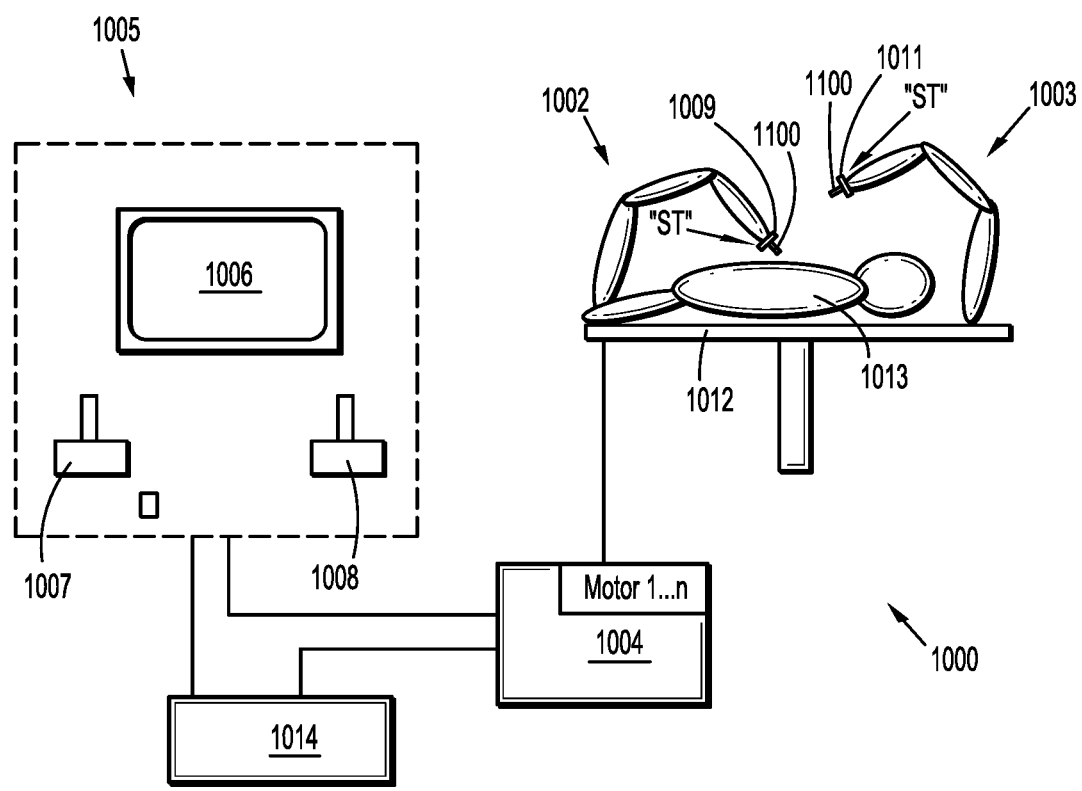
FIG. 23 is a schematic illustration of a robotic surgical system configured for use in accordance with the present disclosure.

Referring to FIG. 23, a medical work station is shown generally as work station 1000 and generally may include a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person (not shown), for example a surgeon, may be able to telemanipulate robot arms 1002, 1003 in a first operating mode.

Each of the robot arms 1002, 1003 may include a plurality of members, which are connected through joints, and an attaching device 1009, 1011, to which may be attached, for example, a surgical tool "ST" supporting an end effector 1100, in accordance with any one of several embodiments disclosed herein, as will be described in greater detail below.

Robot arms 1002, 1003 may be driven by electric drives (not shown) that are connected to control device 1004. Control device 1004 (e.g., a computer) may be set up to activate the drives, in particular by means of a computer program, in such a way that robot arms 1002, 1003, their attaching devices 1009, 1011 and thus the surgical tool (including end effector 1100) execute a desired movement according to a movement defined by means of manual input devices 1007, 1008. Control device 1004 may also be set up in such a way that it regulates the movement of robot arms 1002, 1003 and/or of the drives.

Medical work station 1000 may be configured for use on a patient 1013 lying on a patient table 1012 to be treated in a minimally invasive manner by means of end effector 1100. Medical work station 1000 may also include more than two robot arms 1002, 1003, the additional robot arms likewise being connected to control device 1004 and being telemanipulatable by means of operating console 1005. A medical instrument or surgical tool (including an end effector 1100) may also be attached to the additional robot arm. Medical work station 1000 may include a database 1014, in particular coupled to with control device 1004, in which are stored, for example, pre-operative data from patient/living being 1013 and/or anatomical atlases.

Reference is made herein to U.S. Pat. No. 8,828,023, the entire content of which is incorporated herein by reference, for a more detailed discussion of the construction and operation of an exemplary robotic surgical system.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. A reposable surgical clip applier, comprising:
a handle assembly, including:
   a housing;
   at least one handle extending from the housing and movable relative to the housing between a spaced-apart position and an approximated position; and
   an inner actuation assembly extending from the housing and operably coupled to the at least one handle, the inner actuation assembly including:
      a proximal drive member movable through the housing;
      a proximal pusher bar movable through the proximal drive member; and
      a handle spring assembly having at least one spring arm engaging the at least one handle to bias the at least one handle towards the spaced-apart position, wherein movement of the at least one handle relative to the housing is configured to move the proximal drive member and the proximal pusher bar in relative opposing directions;
a shaft assembly releasably engagable with the handle assembly, the shaft assembly including:
   an outer tube;
   a jaw assembly supported at a distal end portion of the outer tube; and
   an inner drive assembly slidably disposed within the outer tube and operably coupled to the jaw assembly such that distal movement of the inner drive assembly through the outer tube actuates the jaw assembly; and
a clip cartridge assembly releasably engagable within the shaft assembly, the clip cartridge assembly retaining a stack of surgical clips therein and including:
   a distal pusher operably coupled to a distal-most surgical clip of the stack of surgical clips such that distal movement of the distal pusher loads the distal-most surgical clip into the jaw assembly when the clip cartridge assembly is releasably engaged within the shaft assembly;
   a biasing member configured to bias the distal pusher proximally; and
   a cartridge housing having a support base configured to support at least a portion of the distal pusher, the support base including a distal bridge portion and a proximal bridge portion, wherein the biasing member of the cartridge assembly is operably coupled to the distal pusher and to the proximal bridge portion to bias the distal pusher proximally,
wherein, when the shaft assembly is releasably engaged with the handle assembly and the clip cartridge assembly is releasably engaged within the shaft assembly:
   the proximal drive member is positioned proximally adjacent the inner drive assembly such that movement of the at least one handle towards the approximated position actuates the jaw assembly, and the proximal pusher bar is positioned proximally adjacent the distal pusher such that movement of the at least one handle towards the spaced-apart position loads the distal-most surgical clip into the jaw assembly.

2. The reposable surgical clip applier according to claim 1, wherein the handle spring assembly includes a transverse body portion releasably retained within a proximal end portion of the housing, the transverse body portion defining a bore configured to be in communication with the outer tube of the shaft assembly such that, the proximal drive member is movable through the bore of the handle spring assembly to engage the inner drive assembly of the shaft assembly upon movement of the at least one handle.

3. The reposable surgical clip applier according to claim 2, wherein the at least one spring arm of the handle spring assembly extends outwardly from the transverse body portion and includes a free proximal end portion, the free proximal end portion of the at least one spring arm slidable along the at least handle upon movement of the at least one handle.

4. The reposable surgical clip applier according to claim 1, wherein the housing includes at least one internal feature defining a pivot recess configured to movably receive a distal end portion of the at least one handle, the pivot recess and the at least one handle being sized and configured to cooperate to limit movement of the at least one handle beyond a predetermined approximated position and beyond a predetermined spaced-apart position.

5. The reposable surgical clip applier according to claim 1, wherein movement of the at least one handle towards the approximated position moves the proximal drive member distally about the proximal pusher bar and moves the proximal pusher bar proximally about and through the proximal drive member, and wherein movement of the at least one handle towards the spaced-apart position moves the proximal drive member proximally about the proximal pusher bar and moves the proximal pusher bar distally about and through the proximal drive member.

6. The reposable surgical clip applier according to claim 1, wherein the housing of the handle assembly includes an open distal end portion defining a central passageway and a protrusion extending inwardly into the central passageway, and wherein the shaft assembly includes a tubular proximal segment defining a slot configured to receive the protrusion upon insertion of the tubular proximal segment into the open distal end portion to releasably engage the shaft assembly with the handle assembly.

7. The reposable surgical clip applier according to claim 6, wherein the shaft assembly further includes an inner bushing disposed between the tubular proximal segment and the inner drive assembly, the inner bushing including a slot configured to be axially aligned with the slot of the tubular proximal segment when the inner bushing is disposed therein, such that, the protrusion extending inwardly from the housing is received within the slot of the tubular proximal segment and the slot of the inner bushing.

8. The reposable surgical clip applier according to claim 1, wherein the handle assembly includes a pair of handles pivotably coupled to the housing and extending from opposed sides thereof.

9. The reposable surgical clip applier according to claim 8, wherein the handle spring assembly includes a transverse body portion releasably retained within a proximal end portion of the housing and a pair of spring arms extending outwardly from opposing sides of the transverse body portion, each spring arm of the pair of spring arms configured to engage a respective handle of the pair of handles to bias the pair of handles towards the spaced-apart position.

10. The reposable surgical clip applier according to claim 9, wherein the pair of spring arms each includes a free proximal end portion configured to slide along the respective handle of the pair of handles upon movement of the pair of handles.

11. The reposable surgical clip applier according to claim 8, wherein the handle assembly further includes a linkage assembly configured to pivotably couple the pair of handles to the inner actuation assembly, the linkage assembly having a first link arm configured to operably couple a first handle of the pair of handles to the proximal drive member and a second link arm configured to operably couple a second handle of the pair of handles to the proximal pusher bar, wherein upon movement of the pair of handles towards the approximated position, the first link arm is configured to move the proximal drive member distally and the second link arm is configured to move the proximal pusher bar proximally, and wherein upon movement of the pair of handles towards the spaced-apart position, the first link arm is configured to move the proximal drive member proximally and the second link arm is configured to move the proximal pusher bar distally.

12. The reposable surgical clip applier according to claim 11, wherein the linkage assembly is configured to move the proximal drive member concurrently with the proximal pusher bar upon movement of the pair of handles.

13. The reposable surgical clip applier according to claim 11, wherein the linkage assembly further includes a third link arm configured to operably couple the second handle of the pair of handles to the proximal drive member and a fourth link arm configured to operably couple the first handle of the pair of handles to the proximal pusher bar.

14. The reposable surgical clip applier according to claim 13, wherein the proximal pusher bar is configured to move between the first link arm and the third link arm as the proximal pusher bar moves through the proximal drive member.

15. A reposable surgical clip applier, comprising:
a handle assembly, including:
a housing;
at least one handle extending from the housing and movable relative to the housing between a spaced-apart position and an approximated position; and
an inner actuation assembly extending from the housing and operably coupled to the at least one handle, the inner actuation assembly including:
a proximal drive member movable through the housing;
a proximal pusher bar movable through the proximal drive member; and
a handle spring assembly having at least one spring arm engaging the at least one handle to bias the at least one handle towards the spaced-apart position, wherein movement of the at least one handle relative to the housing is configured to move the proximal drive member and the proximal pusher bar in relative opposing directions;
a shaft assembly releasably engagable with the handle assembly, the shaft assembly including:
an outer tube;
a jaw assembly supported at a distal end portion of the outer tube; and
an inner drive assembly slidably disposed within the outer tube and operably coupled to the jaw assembly such that distal movement of the inner drive assembly through the outer tube actuates the jaw assembly; and a clip cartridge assembly releasably engagable within the shaft assembly, the clip cartridge assembly retaining a stack of surgical clips therein and including:
- a distal pusher operably coupled to a distal-most surgical clip of the stack of surgical clips such that distal movement of the distal pusher loads the distal-most surgical clip into the jaw assembly when the clip cartridge assembly is releasably engaged within the shaft assembly;
- a biasing member configured to bias the distal pusher proximally; and
- a clip carrier including a pair of engagement flanges, and wherein the cartridge housing includes a pair of internal grooves extending longitudinally along at least a portion of a length of the cartridge housing, the pair of internal grooves configured to laterally receive the pair of engagement flanges, respectively, to inhibit axial movement of the clip carrier relative to the cartridge housing, wherein, when the shaft assembly is releasably engaged with the handle assembly and the clip cartridge assembly is releasably engaged within the shaft assembly:
- the proximal drive member is positioned proximally adjacent the inner drive assembly such that movement of the at least one handle towards the approximated position actuates the jaw assembly, and
- the proximal pusher bar is positioned proximally adjacent the distal pusher such that movement of the at least one handle towards the spaced-apart position loads the distal-most surgical clip into the jaw assembly.

16. The reposable surgical clip applier according to claim 15, wherein the clip cartridge assembly further includes a carrier lock disposed proximally adjacent a proximal end portion of the clip carrier, the carrier lock including a pair of opposing arms configured to biasingly engage a pair of opposing internal walls of the cartridge housing, wherein the carrier lock is configured to inhibit proximal movement of the clip carrier relative to the cartridge housing beyond the carrier lock.

* * * * *